(12) United States Patent
Vidyasagar et al.

(10) Patent No.: US 12,109,191 B2
(45) Date of Patent: Oct. 8, 2024

(54) MATERIALS AND METHODS FOR INHIBITING TUMOR GROWTH

(71) Applicants: University of Florida Research Foundation, Incorporated, Gainesville, FL (US); AmiLyfe, LLC, Norwood, MA (US)

(72) Inventors: Sadasivan Vidyasagar, Gainesville, FL (US); Reshu Gupta, Gainesville, FL (US); Stephen Gatto, Norwood, MA (US)

(73) Assignees: AmiLyfe, LLC, Norwood, MA (US); University of Florida Research Foundation, Incorporated, Gainesville, FL (US)

(*) Notice: Subject to any disclaimer, the term of this patent is extended or adjusted under 35 U.S.C. 154(b) by 905 days.

(21) Appl. No.: 16/652,973

(22) PCT Filed: Oct. 2, 2018

(86) PCT No.: PCT/US2018/054015
§ 371 (c)(1),
(2) Date: Apr. 1, 2020

(87) PCT Pub. No.: WO2019/070750
PCT Pub. Date: Apr. 11, 2019

(65) Prior Publication Data
US 2020/0323820 A1    Oct. 15, 2020

Related U.S. Application Data

(60) Provisional application No. 62/566,787, filed on Oct. 2, 2017.

(51) Int. Cl.
*A61K 31/401* (2006.01)
*A61K 31/198* (2006.01)
*A61P 35/00* (2006.01)

(52) U.S. Cl.
CPC .......... *A61K 31/401* (2013.01); *A61K 31/198* (2013.01); *A61P 35/00* (2018.01)

(58) Field of Classification Search
None
See application file for complete search history.

(56) References Cited

U.S. PATENT DOCUMENTS

| 5,658,895 A | 8/1997 | Aoi et al. |
| 2005/0176807 A1* | 8/2005 | Friesen ............... A61P 19/02 |
| | | 514/561 |

FOREIGN PATENT DOCUMENTS

| EP | 1789033 | * | 5/2007 |
| JP | 01-301619 A | | 12/1989 |
| JP | 03-068514 A | | 3/1991 |
| JP | 06-040900 A | | 2/1994 |
| JP | 06-256184 A | | 9/1994 |
| JP | 2005097280 A | | 4/2005 |
| WO | 1993006934 A1 | | 4/1993 |
| WO | 2015003021 A2 | | 1/2015 |
| WO | 2017053328 A1 | | 3/2017 |

OTHER PUBLICATIONS

Seo et al., Diethylstilbestrol, a Novel ANO1 Inhibitor, Exerts an Anticancer Effect on Non-Small Cell Lung Cancer via Inhibition of ANO1. Internal Journal of Molecular Sciences, 2021, 22, p. 1-13.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Notice of opposition to EP Patent No. EP2968241 mailed Jul. 29, 2019 (20 pages).
D M B Boedtkjer et al, "New selective inhibitors of calcium-activated chloride channels—T16A inh-A01, CaCC inh-A01 and MONNA—what do they inhibit?: CaCC inhibitors relax arteries in chloride-free conditions", British Journal of Pharmacology, vol. 172, No. 16, Jul. 8, 2015 (Jul. 8, 2015), p. 4158-4172.
Yohan Seo et al, "Inhibition of ANO1 by luteolin and its cytotoxicity in human prostate cancer PC-3 cells", Plos One, vol. 12, No. 3, Mar. 31, 2017 (Mar. 31, 2017), p. 1-15.
Yohan Seo et al, "Ani9, A Novel Potent Small-Molecule ANO1 Inhibitor with Negligible Effect on ANO2", Plos One, vol. 11, No. 5, May 24, 2016 (May 24, 2016), p. 1-16.

* cited by examiner

*Primary Examiner* — Po-Chih Chen
(74) *Attorney, Agent, or Firm* — Greenberg Traurig, LLP

(57) ABSTRACT

The subject invention provides compositions and methods for inhibiting the growth and/or proliferation of cancer cells. The subject invention also provides methods for treating cancer in a subject in need of such treatment by administering a composition described herein. The subject invention can be used to inhibit cancer cell growth by exposing the cells to a composition. The subject invention further provides cancer treatments that may be used in combination with surgery, chemotherapy, and/or radiation therapy.

12 Claims, 16 Drawing Sheets

HT-29 cells 4 Hour treatment

Control                         7AA-Ano1

MATERIALS AND METHODS FOR INHIBITING TUMOR GROWTH

RELATED APPLICATIONS

This application claims priority under 35 U.S.C. § 119(e) to U.S. Provisional Application, U.S. Ser. No. 62/566,787, filed Oct. 2, 2017, which is incorporated herein by reference.

BACKGROUND OF THE INVENTION

Cancer is one of the leading causes of death for both men and women in the United States and around the world. The leading causes of cancer death include lung cancer, colorectal cancer, pancreatic cancer, and breast cancer.

Early detection of cancer is a key to improving survival. Studies indicate that cancer detection in an early, localized stage and surgical removal of such disease increases the five-year survival rate. However, the survival rate declines dramatically after the cancer has spread to other organs, especially to distant sites. Unfortunately, some cancers including lung cancer are usually asymptomatic until they have reached an advanced stage.

Treatment and prognosis depend upon the type of cancer and the stage (degree of spread). Possible treatment modalities include surgery, chemotherapy, and/or radiotherapy. Radiation and/or chemotherapy can cause severe damage to the lining of the gastrointestinal (GI) tract. Moderate to high doses of radiation and/or chemotherapy result in the destruction of cells with clonogenic potential, which are essential for the continuous replacement of cells that are shed from the top of the villi during the normal proliferation, maturation, and differentiation process. The crypt to the villus migration takes between 5-7 days. Therefore, gastrointestinal toxicity manifests itself in the first week following radiation exposure and /or chemotherapy and is the most significant dose-limiting factor in cancer therapy.

The anoctamin (ANO, also known as TMEM16) protein family, which consists of 10 members (ANO1-10) in mammals, is a family of transmembrane proteins having $Ca^{2+}$-activated Cl-activity. ANO proteins play a role in various diseases including cancer. It has been reported that ANO1 (also known as TMEM16a) is upregulated in gastrointestinal stromal tumor, as well as in oral carcinoma and head and neck squamous cell carcinoma. Anoctamin 1 (Ano1, TMEM16A) is a novel Ca2+-activated chloride channel (CaCC) with important physiological functions in epithelial cells and other cell types. The coding sequence of Ano1 is located within the 11q13 region, a chromosomal locus that is frequently amplified in a number of different human cancers, such as urinary bladder cancer, breast cancer and HNSCC. It has been also reported that ANO5 (also known as TMEM16e) mutations in humans cause gnathodiaphyseal dysplasia. In addition, it has been reported that ANO7 (also known as TMEM16g) is selectively expressed in normal and cancerous prostates and regulates cell-cell aggregation.

As described in U.S. patent application Ser. No. 14/406,087, filed Dec. 5, 2014, which is incorporated herein, in its entirety, by reference, anoctamin proteins are also associated with radiation toxicity caused by radiation therapy, a common treatment regime for cancer. One composition useful for the treatment of radiation enteritis is an amino acid-based oral rehydration solution (AA-ORS) described in U.S. Pat. No. 8,993,522, which is incorporated herein, in its entirety, by reference. The formulation used in U.S. Pat. No. 8,993,522 works by correcting rehydration via amino acid-coupled sodium transport, decreasing anion secretion from the crypt by choosing a set of amino acids with anti-secretory property, and by tightening the mucosa.

Despite advances in surgery, chemotherapy, and radiation therapy, a need exists for the development of novel therapies for cancer treatment, particularly those which are efficacious, cost-effective, and improve patient tolerance.

SUMMARY OF THE INVENTION

Provided herein are compositions for inhibiting cancer cell growth and/or proliferation comprising, consisting essentially of, or consisting of one or more free amino acids selected from proline, serine, threonine, tyrosine, valine, asparagine, glycine, tryptophan, lysine, leucine, phenylalanine, methionine, arginine, histidine, and cysteine, and optionally a pharmaceutically acceptable carrier, buffer, electrolyte, or excipient. In certain embodiments, the composition comprises, consists essentially of, or consists of two or more, three or more, four or more, five or more, six or more, seven or more, eight or more, nine or more, ten or more, eleven or more, twelve or more, thirteen or more, fourteen or more, or all fifteen free amino acids selected from proline, serine, threonine, tyrosine, valine, asparagine, glycine, tryptophan, lysine, leucine, phenylalanine, methionine, arginine, histidine, and cysteine.

In certain embodiments, the composition comprises, consists essentially of, or consists of one or more free amino acids selected from proline, serine, threonine, tyrosine, and valine. In certain embodiments, the composition comprises, consists essentially of, or consists of two or more, three or more, four or more, or all five free amino acids selected from proline, serine, threonine, tyrosine, and valine. In certain embodiments, the composition further comprises the free amino acid asparagine. In certain embodiments, the composition further comprises the free amino acid glycine. In certain embodiments, the composition further comprises the free amino acids asparagine and glycine. In certain embodiments, the composition comprises, consists essentially of, or consists of one or more free amino acids selected from asparagine, glycine, valine, proline, serine, threonine, and tyrosine. In certain embodiments, the composition comprises, consists essentially of, or consists of two or more, three or more, four or more, five or more, six or more, or all seven free amino acids selected from asparagine, glycine, valine, proline, serine, threonine, and tyrosine. In certain embodiments, the composition further comprises water. In certain embodiments, the composition further comprises a pharmaceutically acceptable carrier, buffer, electrolyte, or adjuvant.

Also provided herein are methods of treating cancer or a tumor comprising administering to a subject in need thereof a therapeutically effective amount of a composition comprising, consisting essentially of, or consisting of one or more free amino acids selected from proline, serine, threonine, tyrosine, valine, asparagine, glycine, tryptophan, lysine, leucine, phenylalanine, methionine, arginine, histidine, and cysteine, and optionally a pharmaceutically acceptable carrier, buffer, electrolyte, adjuvant, or excipient.

Further disclosed herein are methods of inhibiting cancer cell growth, the method comprising exposing cancer cells to a composition comprising, consisting essentially of, or consisting of one or more free amino acids selected from proline, serine, threonine, tyrosine, valine, asparagine, glycine, tryptophan, lysine, leucine, phenylalanine, methionine, arginine, histidine, and cysteine, and optionally a pharmaceutically acceptable, carrier, buffer, electrolyte, adjuvant, or excipient.

In another aspect, the present disclosure provides compositions comprising, consisting essentially of, or consisting of one or more free amino acids selected from proline, serine, threonine, tyrosine, valine, asparagine, glycine, tryptophan, lysine, leucine, phenylalanine, methionine, arginine, histidine, and cysteine for use in treating cancer. In a further aspect, the present invention provides use of the compositions of amino acids to treat cancer in a subject in need thereof.

BRIEF DESCRIPTION OF THE DRAWINGS

FIG. 10A shows the number of colonies as part of the effects of a control plasmid vector pSV and ANO1 siRNA in normal intestine cells (CRL-1831). FIG. 10B shows the number of colonies as part of the effects of a control plasmid vector pSV and ANO1 siRNA in Caco2 cancer cells and the number of colonies with pSV and SiAno1. pSV indicates the control vector transfected: 6 wells in the plate seeded with caco2 cells with increasing density. SiANO1 caco-2 indicates: small inhibitory RNA specific for ANO1 used to inhibit ANO1 synthesis and expression.

" FIG. 12C shows the net flux of Cl-following exposure of 5Gy of radiation and treatment with "ANO7AA," at basal levels, CaCCinh, and "ANO1." Ussing chamber flux studies show that specific inhibitor of ANO1 (CaCCinh) decreased net chloride flux and the 7 amino acids that decreased ano1 expression (ANO7AA) on the membrane similarly decreased net chloride flux. The flux was studied using 36Cl an isotope for chloride.

In FIGS. 13A-13D, flow cytometry (FACS) was conducted using cells incubated in the presence of regular ringer solution ("RR"), 5AA, and 7AA. The results shown in FIGS. 13A-13D show that 7AA inhibits the cells in G2/M phase and therefore there are more cell numbers arrested in G1 phase (FIG. 13D). FIG. 13A shows the effects (cell count) of a 4 hour treatment of the amino acid composition "RR" on colon cancer cells (HT-29). FIG. 13B shows the effects (cell count) of a 4 hour treatment of the amino acid composition "5AA" on colon cancer cells (HT-29). FIG. 13C shows the effects (cell count) of a 4 hour treatment of the amino acid composition "7AA" on colon cancer cells (HT-29). FIG. 13D shows the effects of a 4 hour treatment of the control and the amino acid compositions "5AA" and "7AA" on colon cancer cells (HT-29), and on the number of cells present in the phases G1, S, and G2/M in the cell cycle.

DETAILED DESCRIPTION OF CERTAIN EMBODIMENTS

Figure 1:
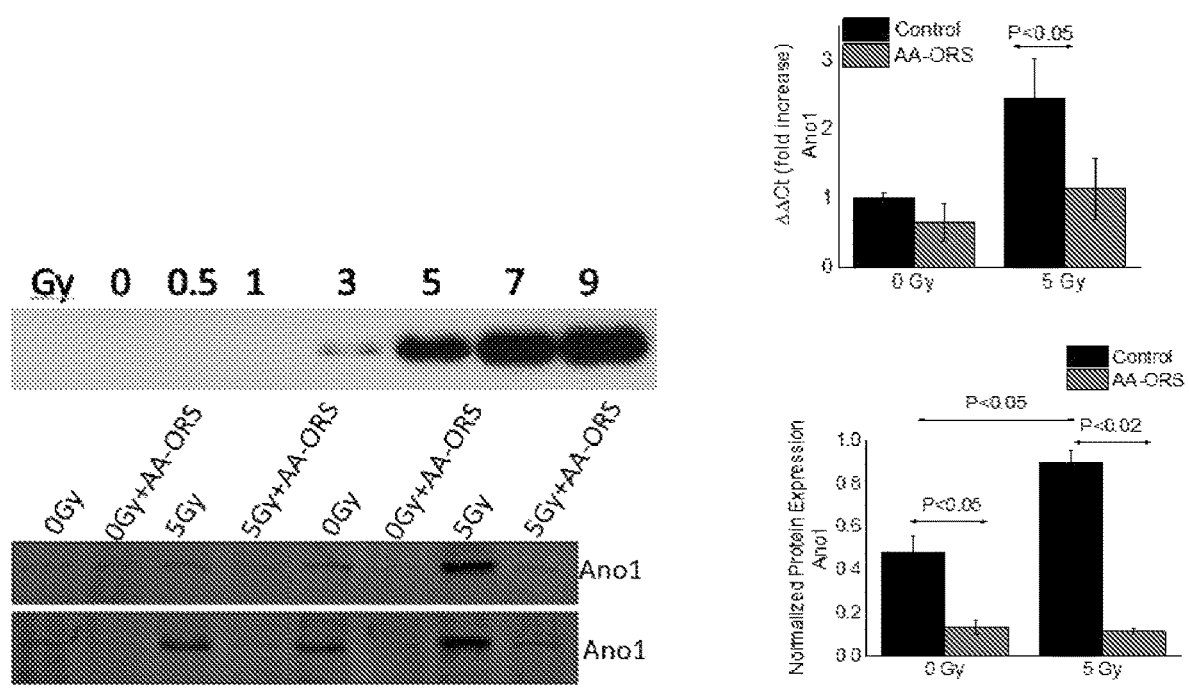
FIG. 1 shows a Western blots analysis of anocatmin-1 (ANO1) protein levels following exposure to 0, 0.5, 1, 3, 5, 7 and 9 Gy of radiation (top left) and following exposure to 0 and 5 Gy of radiation (bottom left) in the presence and absence of an amino acid oral rehydration solution (AA-ORS). The figure on top right shows ano1 mRNA levels with radiation in the presence absence of treatment.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

The terms "a" and "an" and "the" and similar referents as used in the context of describing the invention are to be construed to cover both the singular and the plural, unless otherwise indicated herein or clearly contradicted by context.

Various terms relating to aspects of the description are used throughout the specification and claims. Such terms are to be given their ordinary meaning in the art unless otherwise indicated. Other specifically defined terms are to be construed in a manner consistent with the definitions provided herein.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Therapeutic Compositions

Provided herein are compositions for inhibiting cancer cell growth and/or proliferation comprising one or more free amino acids selected from proline, serine, threonine, tyrosine, valine, asparagine, glycine, tryptophan, lysine, leucine, phenylalanine, methionine, arginine, histidine, and cysteine, and a pharmaceutically acceptable excipient.

"Pharmaceutically acceptable excipient" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, stearates, silicon dioxide, polyvinyl alcohols, talc, titanium dioxide, ferric oxide, and polyethylene glycols.

In one embodiment, the compositions for inhibiting cancer cell growth and/or proliferation comprises, or consists essentially of, only one free amino acid selected from proline, serine, threonine, tyrosine, valine, asparagine, glycine, tryptophan, lysine, leucine, phenylalanine, methionine, arginine, histidine, and cysteine, and optionally a pharmaceutically acceptable carrier, buffer, electrolyte, adjuvant, or excipient. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In a further embodiment, the composition comprises, or consists essentially of, proline as a free amino acid. In a further embodiment, the composition comprises, or consists essentially of, serine as a free amino acid. In a further embodiment, the composition comprises, or consists essentially of, threonine as a free amino acid. In a further embodiment, the composition comprises, or consists essentially of, tyrosine as a free amino acid. In a further embodiment, the composition comprises, or consists essentially of, valine as a free amino acid. In a further embodiment, the composition comprises, or consists essentially of, asparagine as a free amino acid. In a further embodiment, the composition comprises, or consists essentially of, glycine as a free amino acid. In a further embodiment, the composition comprises, or consists essentially of, tryptophan as a free amino acid. In a further embodiment, the composition comprises, or consists essentially of, lysine as a free amino acid. In a further embodiment, the composition comprises, or consists essentially of, leucine as a free amino acid. In a further embodiment, the composition comprises, or consists essentially of, phenylalanine as a free amino acid. In a further embodiment, the composition comprises, or consists essentially of, methionine as a free amino acid. In a further embodiment, the composition comprises, or consists essentially of, arginine as a free amino acid. In a further embodiment, the composition comprises, or consists essentially of, histidine as a free amino acid. In a further embodiment, the composition comprises, or consists essentially of, cysteine as a free amino acid.

In another embodiment, the compositions for inhibiting cancer cell growth and/or proliferation comprises, consists essentially of, or consists of any two free amino acids selected from proline, serine, threonine, tyrosine, valine, asparagine, glycine, tryptophan, lysine, leucine, phenylalanine, methionine, arginine, histidine, and cysteine, including, but not limited to, the combination of proline and serine, the combination of proline and threonine, the combination of proline and tyrosine, the combination of proline and valine, the combination of proline and asparagine, the combination of proline and glycine, the combination of proline and tryptophan, the combination of proline and lysine, the combination of proline and leucine, the combination of proline and phenylalanine, the combination of proline and methionine, the combination of proline and arginine, the combination of proline and histidine, the combination of proline and cysteine, the combination of serine and threonine, the combination of serine and tyrosine, the combination of serine and valine, the combination of serine and asparagine, the combination of serine and glycine, the combination of serine and tryptophan, the combination of serine and lysine, the combination of serine and leucine, the combination of serine and phenylalanine, the combination of serine and methionine, the combination of serine and arginine, the combination of serine and histidine, the combination of serine and cysteine, the combination of threonine and tyrosine, the combination of threonine and valine, the combination of threonine and asparagine, the combination of threonine and glycine, the combination of threonine and tryptophan, the combination of threonine and lysine, the combination of threonine and leucine, the combination of threonine and phenylalanine, the combination of threonine and methionine, the combination of threonine and arginine, the combination of threonine and histidine, the combination of threonine and cysteine, the combination of tyrosine and valine, the combination of tyrosine and asparagine, the combination of tyrosine and glycine, the combination of tyrosine and tryptophan, the combination of tyrosine and lysine, the combination of tyrosine and leucine, the combination of tyrosine and phenylalanine, the combination of tyrosine and methionine, the combination of tyrosine and arginine, the combination of tyrosine and histidine, the combination of tyrosine and cysteine, the combination of valine and asparagine, the combination of valine and glycine, the combination of valine and tryptophan, the combination of valine and lysine, the combination of valine and leucine, the combination of valine and phenylalanine, the combination of valine and methionine, the combination of valine and arginine, the combination of valine and histidine, the combination of valine and cysteine, the combination of asparagine and glycine, the combination of asparagine and tryptophan, the combination of asparagine and lysine, the combination of asparagine and leucine, the combination of asparagine and phenylalanine, the combination of asparagine and methionine, the combination of asparagine and arginine, the combination of asparagine and histidine, the combination of asparagine and cysteine, the combination of glycine and tryptophan, the combination of glycine and lysine, the combination of glycine and leucine, the combination of glycine and phenylalanine, the combination of glycine and methionine, the combination of glycine and arginine, the combination of glycine and histidine, the combination of glycine and cysteine, the combination of tryptophan and lysine, the combination of tryptophan and leucine, the combination of tryptophan and phenylalanine, the combination of tryptophan and methionine, the combination of tryptophan and arginine, the combination of tryptophan and histidine, the combination of tryptophan and cysteine, the combination of lysine and leucine, the combination of lysine and phenylalanine, the combination of lysine and methionine, the combination of lysine and arginine, the combination of lysine and histidine, the combination of lysine and cysteine, the combination of leucine and phenylalanine, the combination of leucine and methionine, the combination of leucine and arginine, the combination of leucine and histidine, the combination of leucine and cysteine, the combination of phenylalanine and methionine, the combination of phenylalanine and arginine, the combination of phenylalanine and histidine, the combination of phenylalanine and cysteine, the combination of arginine and histidine, the combination of arginine and cysteine, and the combination of histidine and cysteine. The combinations disclosed in this paragraph are hereby disclosed in further combination with a third, fourth, fifth, sixth, seventh, eighth, ninth, tenth, eleventh, twelfth, and/or thirteenth free amino acid selected from proline, serine, threonine, tyrosine, valine, asparagine, glycine, tryptophan, lysine, leucine, phenylalanine, methionine, arginine, histidine, and cysteine. For the sake of brevity, all of the combinations are not being parsed out.

In another embodiment, the compositions for inhibiting cancer cell growth and/or proliferation comprises, consists essentially of, or consists of any three free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine and threonine, the combination of proline, serine and threonine, including, but not limited to, the combination of proline, serine, and threonine, the combination of proline, serine, and tyrosine, the combination of proline, serine, and valine, the combination of proline, threonine, and tyrosine, the combination of proline, threonine, and valine, the combination of serine, threonine, and tyrosine, the combination of serine, tyrosine, and valine, and the combination of threonine, tyrosine, and valine. For the sake of brevity, all of the combinations are not being parsed out.

In a further embodiment, the compositions for inhibiting cancer cell growth and/or proliferation comprises, consists essentially of, or consists of any four free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine and tyrosine, the combination of proline, serine, threonine and valine, and the combination of serine, threonine, tyrosine and valine. For the sake of brevity, all of the combinations are not being parsed out.

In another embodiment, the compositions for inhibiting cancer cell growth and/or proliferation comprises, consists essentially of, or consists of any five free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, and valine, the combination of asparagine, serine, threonine, tyrosine, and valine, the combination of proline, asparagine, threonine, tyrosine, and valine, the combination of proline, serine, asparagine, tyrosine, and valine, the combination of proline, serine, threonine, asparagine, and valine, the combination of proline, serine, threonine, tyrosine, and asparagine, the combination of glycine, serine, threonine, tyrosine, and valine, the combination of proline, glycine, threonine, tyrosine, and valine, the combination of proline, serine, glycine, tyrosine, and valine, the combination of proline, serine, threonine, glycine, and valine, and the combination of proline, serine, threonine, tyrosine, and glycine. For the sake of brevity, all of the combinations are not being parsed out.

In another embodiment, the compositions for inhibiting cancer cell growth and/or proliferation comprises, consists essentially of, or consists of any six free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, and asparagine, and the combination of proline, serine, threonine, tyrosine, valine, and glycine. For the sake of brevity, all of the combinations are not being parsed out.

In another embodiment, the compositions for inhibiting cancer cell growth and/or proliferation comprises, consists essentially of, or consists of any seven free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, and glycine, the combination of proline, serine, threonine, tyrosine, valine, leucine, and asparagine, and the combination of proline, serine, threonine, tyrosine, valine, leucine, and glycine. For the sake of brevity, all of the combinations are not being parsed out.

In another embodiment, the compositions for inhibiting cancer cell growth and/or proliferation comprises, consists essentially of, or consists of any eight free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, and tryptophan. For the sake of brevity, all of the combinations are not being parsed out.

In another embodiment, the compositions for inhibiting cancer cell growth and/or proliferation comprises, consists essentially of, or consists of any nine free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, and lysine. For the sake of brevity, all of the combinations are not being parsed out.

In another embodiment, the compositions for inhibiting cancer cell growth and/or proliferation comprises, consists essentially of, or consists of any ten free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, and leucine. For the sake of brevity, all of the combinations are not being parsed out.

In another embodiment, the compositions for inhibiting cancer cell growth and/or proliferation comprises, consists essentially of, or consists of any eleven free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, leucine, and phenylalanine. For the sake of brevity, all of the combinations are not being parsed out.

In another embodiment, the compositions for inhibiting cancer cell growth and/or proliferation comprises, consists essentially of, or consists of any twelve free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, leucine, phenylalanine, and methionine. For the sake of brevity, all of the combinations are not being parsed out.

In another embodiment, the compositions for inhibiting cancer cell growth and/or proliferation comprises, consists essentially of, or consists of any thirteen free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, leucine, phenylalanine, methionine, and arginine. For the sake of brevity, all of the combinations are not being parsed out.

In another embodiment, the compositions for inhibiting cancer cell growth and/or proliferation comprises, consists essentially of, or consists of any fourteen free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, leucine, phenylalanine, methionine, arginine, and histidine. For the sake of brevity, all of the combinations are not being parsed out.

In another embodiment, the compositions for inhibiting cancer cell growth and/or proliferation comprises, consists essentially of, or consists of any fifteen free amino acids selected from proline, serine, threonine, tyrosine, valine, asparagine, glycine, tryptophan, lysine, leucine, phenylalanine, methionine, arginine, histidine, and cysteine, including, but not limited to, the combination of proline, serine, threonine, tyrosine, valine, asparagine, glycine, tryptophan, lysine, leucine, phenylalanine, methionine, arginine, histidine, and cysteine.

The compositions of the subject invention may comprise natural amino acids or derivatives thereof that retain substantially the same, or better, activity in terms of inhibiting the growth, proliferation and/or development of cancer cells. The term "amino acid" encompasses all known amino acids comprising an amine (—NH2) functional group, a carboxyl (—COOH) functional group, and a side chain ("R") group specific to each amino acid. "Amino acids" encompasses the 21 amino acids encoded by the human genome (i.e., proteinogenic amino acids), amino acids encoded or produced by bacteria or single-celled organisms, and naturally derived amino acids. For the purposes of this disclosure, the conjugate acid form of amino acids with basic side chains (arginine, lysine, and histidine) or the conjugate base form of amino acids with acidic side chains (aspartic acid and glutamic acid) are essentially the same, unless otherwise noted. "Amino acids" also encompass derivatives thereof that retain substantially the same, or better, activity in terms of enhancing the effect of a composition of the present invention (e.g., increasing the number of CFTR proteins in the plasma membrane, increasing chloride ion export from a cell, treating cystic fibrosis). The derivatives may be, for example, enantiomers, and include both the D- and L-forms of the amino acids. The derivatives may be derivatives of "natural" or "non-natural" amino acids (e.g., (β-amino acids, homo-amino acids, proline derivatives, pyruvic acid derivatives, 3-substituted alanine derivatives, glycine derivatives, ring-substituted tyrosine derivatives, ring-substituted phenylalanine derivatives, linear core amino acids, and N-methyl amino acids), for example, selenocysteine, pyrrolysine, iodotyrosine, norleucine, or norvaline. Other amino acid derivatives include, but are not limited to, those that are synthesized by, for example, acylation, methylation, glycosylation, and/or halogenation of the amino acid. These include, for example, (β-methyl amino acids, C-methyl amino acids, and N-methyl amino acids. The amino acids described herein may be present as free amino acids. The term "free amino acid" refers to an amino acid that is not part of a peptide or polypeptide (e.g., is not connected to another amino acid through a peptide bond). A free amino acid is free in solution, but may be associated with a salt or other component in solution.

In certain embodiments, the compositions for inhibiting cancer cell growth and/or proliferation do not include, or only include negligible amounts of, one or more free amino acids selected from glutamate, glutamine, aspartic acid, alanine, and isoleucine. By "negligible" it is meant that the serine present has no effect on cancer cells inhibition. Or, in certain embodiments, even if these amino acids are present in the composition, they are not present in an amount that would affect the therapeutic effect of inhibiting tumor and/or cancel cell growth. In certain embodiments, a negligible amount is an amount wherein the total concentration of the amino acid is less than 100 mg/l, 50 mg/l, 10 mg/l, 5 mg/l, 1 mg/l, 0.5 mg/l, 0.1 mg/l, or 0.01 mg/l. In certain embodiments, a negligible amount is an amount wherein the total concentration of the amino acid is less than 100 mg/l. In certain embodiments, a negligible amount is an amount wherein the total concentration of the amino acid is less than 50 mg/l. In certain embodiments, a negligible amount is an amount wherein the total concentration of the amino acid is less than 10 mg/l. In certain embodiments, a negligible amount is an amount wherein the total concentration of the amino acid is less than 5 mg/l. In certain embodiments, a negligible amount is an amount wherein the total concentration of the amino acid is less than 1 mg/l. In certain embodiments, a negligible amount is an amount wherein the total concentration of the amino acid is less than 0.5 mg/l. In certain embodiments, a negligible amount is an amount wherein the total concentration of the amino acid is less than 0.1 mg/l. In certain embodiments, a negligible amount is an amount wherein the total concentration of the amino acid is less than 0.01 mg/l.

In one embodiment, the compositions for inhibiting cancer cell growth and/or proliferation do not include, or only includes negligible amounts of, one of the free amino acid selected from glutamate, glutamine, aspartic acid, alanine and isoleucine. In a further embodiment, the composition does not include, or only includes a negligible amount of, glutamate as a free amino acid. In a further embodiment, the composition does not include, or only includes a negligible amount of, glutamine as a free amino acid. In a further embodiment, the composition does not include, or only includes a negligible amount of, aspartic acid as a free amino acid. In a further embodiment, the composition does not include, or only includes a negligible amount of, alanine as a free amino acid. In a further embodiment, the composition does not include, or only includes a negligible amount of, isoleucine as a free amino acid.

In further embodiments, the compositions for inhibiting cancer cell growth and/or proliferation do not include, or only includes negligible amounts of, two of the free amino acid selected from glutamate, glutamine, aspartic acid, alanine and isoleucine, including, but not limited to, the combination of glutamate and glutamine, the combination of glutamate and aspartic acid, the combination of glutamate and alanine, the combination of glutamate and isoleucine, the combination of glutamine and aspartic acid, the combination of glutamine and alanine, the combination of glutamine and isoleucine, the combination of aspartic acid and alanine, the combination of aspartic acid and isoleucine, and the combination of alanine and isoleucine.

In further embodiments, the compositions for inhibiting cancer cell growth and/or proliferation do not include, or only include negligible amounts of, three of the free amino acid selected from glutamate, glutamine, aspartic acid, alanine and isoleucine, including, but not limited to, the combination of glutamate, glutamine, and aspartic acid, the combination of glutamate, glutamine, and alanine, the combination of glutamate, glutamine, and isoleucine, the combination of glutamate, aspartic acid, and alanine, the combination of glutamate, aspartic acid, and isoleucine, the combination of glutamate, alanine, and isoleucine, the combination of glutamine, aspartic acid, and alanine, the combination of glutamine, aspartic acid, and isoleucine, the combination of glutamine, aspartic acid, and isoleucine, and the combination of aspartic acid, alanine, and isoleucine.

In further embodiments, the compositions for inhibiting cancer cell growth and/or proliferation do not include, or only includes negligible amounts of, four of the free amino acid selected from glutamate, glutamine, aspartic acid, alanine and isoleucine, including, but not limited to, the combination of glutamate, glutamine, aspartic acid and alanine, the combination of glutamate, glutamine, aspartic acid, and isoleucine, and the combination of glutamine, aspartic acid, alanine, and isoleucine.

In further embodiments, the compositions for inhibiting cancer cell growth and/or proliferation do not include, or only includes negligible amounts of, five of the free amino acid selected from glutamate, glutamine, aspartic acid, alanine, and isoleucine, including, but not limited to, the combination of glutamate, glutamine, aspartic acid, alanine, and isoleucine.

In certain embodiments, the cancer cells of the subject invention express anoctamin selected from the group consisting of anoctamin-1, anoctamin-2, anoctamin-3, anoctamin-4, anoctamin-5, anoctamin-6, anoctamin-7, anoctamin-8, anoctamin-9, and anoctamin-10, preferably, anoctamin-1 (ANO1), the $Ca^{2+}$-activated $Cl^-$ channel (CaCC).

The level of anoctamin expression can be determined based on mRNA levels or protein levels. Determination of anoctamin expression can be made qualitatively, semi-quantitatively, or quantitatively. Sequences of anoctamin proteins and mRNAs of a variety of mammalian species are publicly available and can be obtained from, for example, the GenBank database. In one embodiment, the human anoctamin-1 (ANO1) protein has the amino acid sequence associated with GenBank Accession No. NP_060513. In another embodiment, the human anoctamin 1 mNRA transcript has the nucleic acid sequence associated with GenBank Accession No. NM_018043. One of ordinary skill in the art, having the benefit of the present disclosure, can easily use anoctamin protein and nucleic acid sequences of a mammalian species of interest to practice the present invention.

Methods for determining anoctamin expression level are well known in the art, including but not limited to, Western blot, enzyme-linked immunosorbent assay (ELISA), immunoprecipitation, polymerase chain reaction (PCR) methods including reverse transcription polymerase chain reaction (RT-PCR), nucleic acid hybridization, and any combination thereof. In a preferred embodiment, the anoctamin expression level is determined using ELISA.

The level of anoctamin (e.g., ANO1) expression can be determined based on anoctamin (e.g., ANO1) mRNA level. In one embodiment, the anoctamin mRNA level can be determined by a method comprising contacting the biological sample with a polynucleotide probe that comprises a nucleic acid sequence that specifically binds to, or hybridizes under stringent conditions with, an anoctamin (e.g., ANO1) mRNA; and detecting the complex formed between the polynucleotide probe and the anoctamin (e.g., ANO1) mRNA.

In one embodiment, the anoctamin mRNA level can be determined by polymerase chain reaction methods. Polymerase chain reaction (PCR) is a process for amplifying one or more target nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. The skilled artisan, to detect the presence of a desired sequence (U.S. Pat. No. 4,683,195), routinely uses polymerase chain reaction.

In one embodiment, the composition according to the subject invention inhibits the growth of cancer cells as evidenced by the down-regulation of ANO1.

In preferred embodiments, the cancer cells of the subject invention are brain tumor cells, nasopharyngeal carcinoma cells, breast cancer cells, lung cancer cells, abnormal leukocytes, abnormal lymphocytes, colon cancer cells, liver cancer cells, stomach cancer cells, esophageal cancer cells, bladder cancer cells, or skin cancer cells.

In certain embodiments, the one or more free amino acids are at a concentration of from about 0.1 to 2.0 grams/liter in the composition. In one embodiment, proline is at a concentration of from about 0.1 to 2.0 grams/liter. In one embodiment, serine is at a concentration of from about 0.1 to 2.0 grams/liter. In one embodiment, threonine is at a concentration of from about 0.1 to 2.0 grams/liter. In one embodiment, tyrosine is at a concentration of from about 0.1 to 2.0 grams/liter. In one embodiment, valine is at a concentration of from about 0.1 to 2.0 grams/liter. In one embodiment, asparagine is at a concentration of from about 0.1 to 2.0 grams/liter. In one embodiment, glycine is at a concentration of from about 0.1 to 2.0 grams/liter. In one embodiment, tryptophan is at a concentration of from about 0.1 to 2.0 grams/liter. In one embodiment, lysine is at a concentration of from about 0.1 to 2.0 grams/liter. In one embodiment, leucine is at a concentration of from about 0.1 to 2.0 grams/liter. In one embodiment, phenylalanine is at a concentration of from about 0.1 to 2.0 grams/liter. In one embodiment, methionine is at a concentration of from about 0.1 to 2.0 grams/liter. In one embodiment, arginine is at a concentration of from about 0.1 to 2.0 grams/liter. In one embodiment, histidine is at a concentration of from about 0.1 to 2.0 grams/liter. In one embodiment, cysteine is at a concentration of from about 0.1 to 2.0 grams/liter.

In other embodiments, the compositions for inhibiting cancer cell growth and/or proliferation do not include, or include negligible amounts of glutamate, wherein the total concentration of glutamate is less than 100 mg/l, 50 mg/l, 10 mg/l, 5 mg/l, 1 mg/l, 0.5 mg/l, 0.1 mg/l, or 0.01 mg/l. The therapeutic composition may not include, or may include negligible amounts of glutamine, wherein the total concentration of glutamine is less than 100 mg/l, 50 mg/l, 10 mg/l, 5 mg/l, 1 mg/l, 0.5 mg/l, 0.1 mg/l, or 0.01 mg/l. The therapeutic composition may not include, or may include negligible amounts of aspartic acid, wherein the total concentration of aspartic acid is less than 100 mg/l, 50 mg/l, 10 mg/l, 5 mg/l, 1 mg/l, 0.5 mg/l, 0.1 mg/l, or 0.01 mg/l. The therapeutic composition may not include, or may include negligible amounts of alanine, wherein the total concentration of alanine is less than 100 mg/l, 50 mg/l, 10 mg/l, 5 mg/l, 1 mg/l, 0.5 mg/l, 0.1 mg/l, or 0.01 mg/l. The therapeutic composition may not include, or may include negligible amounts of isoleucine, wherein the total concentration of isoleucine is less than 100 mg/l, 50 mg/l, 10 mg/l, 5 mg/l, 1 mg/l, 0.5 mg/l, 0.1 mg/l, or 0.01 mg/l.

In certain embodiments, the compositions for inhibiting cancer cell growth and/or proliferation further comprise at least one additional active agent. The term "agent" is used herein to refer to any substance, compound (e.g., molecule), supramolecular complex, material, or combination or mixture thereof. A compound may be any agent that can be represented by a chemical formula, chemical structure, or sequence. Example of agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. The term "agent" may also encompass a "therapeutic agent". The term "compound" and "agent" may be used interchangeably. In some embodiments, the at least one additional active agent is known to be effective for treating cancer. The compositions can also be formulated in combination with at least one other agent, such as stabilizing or buffer compounds, which can be administered in any sterile, biocompatible pharmaceutical carrier, including, but not limited to, saline, buffered saline, dextrose, and water. In addition to the critical components of compositions discussed herein, cells or influencing factors, the compositions can contain suitable pharmaceutically acceptable carriers comprising excipients and auxiliaries that facilitate processing of the active compounds into preparations that can be used pharmaceutically. The composition may be prepared as a single-dosage form using a pharmaceutically acceptable carrier or excipient or may be contained in a multiple-dosage container.

In certain embodiments, the therapeutic composition comprises one or more electrolytes selected from, for example, $Na^+$; $K^+$; $HCO_3^-$; $CO_3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the composition does not contain $HCO_3^-$ or $CO_3^{2-}$. In another alternative embodiment, the composition comprises $HCO_3^-$ and $CO_3^{2-}$ at a total concentration of less than 5 mg/l, or concentrations lower than 5 mg/l. In certain embodiments, the composition does not contain electrolytes. For example, in certain embodiments the composition does not comprise one or more, or any, of $Na^+$; $K^+$; $HCO_3^-$; $CO_3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum.

In certain embodiments, the composition does not contain one or more of the ingredients selected from oligo-, polysaccharides, and carbohydrates; oligo-, or polypeptides or proteins; lipids; small-, medium-, and/or long-chain fatty acids; and/or food containing one or more above-mentioned nutrients.

In one embodiment, phosphate ions, such as $H_2PO_4^-$, $HPO_4^{2-}$, and $PO_4^{3-}$, are used to buffer the composition of the subject invention. In one embodiment, the therapeutic composition uses $HCO_3^-$ or $CO_3^{2-}$ as a buffer. In another embodiment, the therapeutic composition does not use $HCO_3^-$ or $CO_3^{2-}$ as buffer.

In still further embodiments, the compositions for inhibiting cancer cell growth and/or proliferation have a pH of about 2.0 to about 8.5. For example, the pH of the composition may be 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5.

In certain embodiments, the amino acids of the compositions described herein may be prodrugs of the free amino acids. The term "prodrugs" refers to compounds that have cleavable groups and become by solvolysis or under physiological conditions the compounds described herein, which are pharmaceutically active in vivo.

In certain embodiments, the amino acids of the compositions described herein may be salts of amino acids (i.e., amino acid salts). Amino acids may be in salt form with cations (e.g., salts of amino acids with negatively charged side chains in solution (e.g., glutamate and aspartate)), anions (salts of amino acids with positively charged side chains in solution (e.g., lysine, arginine, histidine)), and inorganic compounds. Exemplary amino acid salts are listed in Fleck M and Petrosyan A M, *Salts of Amino Acids*, 1st Ed; Springer International Publishing, 2014, which is herein incorporated by reference.

In certain embodiments, the composition further comprises water.

In certain embodiments, the composition further comprises a buffer. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

As used herein, the term "salt" refers to any and all salts, and encompasses pharmaceutically acceptable salts.

The term "carrier" may refer to any diluent, adjuvant, excipient, or vehicle with which a composition of the present disclosure is administered. Examples of suitable pharmaceutical carriers are described in Remington's Essentials of Pharmaceuticals, 21st ed., Ed. Felton, 2012, which is herein incorporated by reference.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition. The exact amount of a composition comprising amino acids required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a composition comprising amino acids described herein. In certain embodiments, a dose described herein includes independently between 1 mg and 3 mg, inclusive, of a composition comprising amino acids described herein. In certain embodiments, a dose described herein includes independently between 3 mg and 10 mg, inclusive, of a composition comprising amino acids described herein. In certain embodiments, a dose described herein includes independently between 10 mg and 30 mg, inclusive, of a composition comprising amino acids described herein. In certain embodiments, a dose described herein includes independently between 30 mg and 100 mg, inclusive, of a composition comprising amino acids described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In further embodiments, the compositions for inhibiting cancer cell growth and/or proliferation are in a form of a single unit dose. A "single unit dose" as used herein means the compositions disclosed herein being in a container and in an amount suitable for reconstitution and/or administration of a single dose, wherein the amount suitable for reconstitution and administration of a single dose is a therapeutically effective amount. The single unit dose, although typically in the form of a vial, may be any suitable container, such as ampoules, syringes (e.g., pre-filled syringes), co-vials, cartridges, which are capable of maintaining a sterile environment.

The composition can be administered concurrently with, prior to, or subsequent to one or more additional pharmaceutical agents or therapeutic agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, cancer). In certain embodiments, the additional therapeutic agent is an agent useful for treating cancer. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form. In certain embodiments, a kit described herein further includes instructions for using the kit.

Methods of Treatment

Provided herein are methods of treating cancer or a tumor comprising administering to a subject in need thereof a therapeutically effective amount of the compositions described herein. For example, the compositions may comprise one or more free amino acids selected from proline, serine, threonine, tyrosine, valine, asparagine, glycine, tryptophan, lysine, leucine, phenylalanine, methionine, arginine, histidine, and cysteine, and a pharmaceutically acceptable excipient.

In certain embodiments, the one or more free amino acids comprise, consist essentially of, or consist of proline, serine, threonine, tyrosine, and valine. In other embodiments, the one or more free amino acids comprise, consist essentially of, or consist of proline, serine, threonine, tyrosine, valine, asparagine, and glycine.

In other embodiments, the compositions provided herein do not include one or more free amino acids selected from glutamate, glutamine, aspartic acid, alanine, and isoleucine.

The subject may be a patient in which inhibiting the growth of tumor cells and/or cancer cells is needed. The subject can be any animal, including, for example, a human. In addition to humans, the animal may be, for example, mammals such as cattle, horses, sheep, pigs, goats, dogs, and cats. The animals may also be, for example, chickens, turkeys, or fish. In preferred aspects, the subject is a human.

The term "administer," "administering," or "administration" refers to implanting, absorbing, ingesting, injecting, inhaling, or otherwise introducing a compound described herein, or a composition thereof, in or on a subject.

As used herein, the phrase "therapeutically effective amount" refers to an amount of the compositions, as described herein, effective to achieve a particular biological or therapeutic result such as, but not limited to, biological or therapeutic results disclosed, described, or exemplified herein. The therapeutically effective amount may vary according to factors such as the disease state, age, sex, and weight of the individual, and the ability of the composition to cause a desired response in a subject. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. Exemplary indicators of a therapeutically effect amount include, for example, improved well-being of the patient, reduction of a tumor burden, arrested or slowed growth of a cancer, and/or absence of metastasis of cancer cells to other locations in the body.

In some embodiments, the subject also receives radiation, chemotherapy, proton therapy, a cytotoxic agent, or a combination thereof.

In one embodiment, the subject invention provides a method of improving therapeutic outcomes of chemotherapy and/or radiotherapy in a patient having tumors and/or cancers, comprising administering a therapeutic composition according to the subject invention. The subject invention also provides a maintenance or supportive therapy following, for example, chemotherapy and/or radiotherapy in a patient having tumors and/or cancer.

In one embodiment, the subject or patient has been subjected to radiation prior to treatment with the composition of the subject invention. In some embodiments, the subject was exposed to low dose radiation, for example, during travel to outer space. In some embodiments, the subject was exposed to high dose radiation. In some embodiments, multiple subjects were exposed to radiation from accidental exposure such as through a radiation leak or from intentional exposure such as an weaponized attack. In some embodiments, the subject was exposed to radiation as a preventative medical procedure. In some embodiments, the subject is predisposed to tumor or cancer formation.

In another embodiment, the subject or patient will be subjected to radiation after treatment with the composition of the subject invention. The radiation may be administered to the cancer cells, for example, 1 minute, 5 minutes, 30 minutes, 1 hour, 6 hours, 12 hours, 1 day, 5 days, 30 days, 3 months, 6 months, 1 year, 2 years, or 3 years or more, before or after treatment of the cells with the composition of the subject invention. The dose of radiation may be, for example, at least 1, 2, 3, 4, 5, 6, 7, 8, 9, 10, 15, 20, 25, 30, 35, 40, 45, 50, 55, 60, 65, 70, 80, 85, 90, 95, 100, 120, or 150 Gy.

Additionally, the compositions of the subject invention can be used in the treatment of cancer in a subject who has received chemotherapy. In certain embodiments, the compositions of the subject invention may be administered concurrently with, prior to, or subsequent to, one or more additional therapeutically active agents. In certain embodiments, the additional therapeutic is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ- 26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, hexamethyl melamine, topoisomerase inhibitors (e.g., inhibitors of topoisomerase I or topoisomerase II. Topoisomerase I inhibitors such as irinotecan (CPT-II), aminocamptothecin, camptothecin, DX-8951f, and topotecan. Topoisomerase II inhibitors include etoposide (VP-16), and teniposide (VM-26)), Thiotepa, bysulfan, oxyplatin, leucourin (LU),vinblastine, epothilone, pegylated adriamycin, vindesine, neocarzinostatin, cis-platinum, 5-fluorouridine, ibrutinib, and calicheamicin, and/or a combination thereof.

In certain aspects, the cancer or tumor treated by the methods and compositions disclosed herein expresses anoctamin (ANO). In certain embodiments, the anoctamin (ANO) is anoctamin-1 (ANO1). In certain embodiments, the anoctamin is anoctamin-2 (ANO2). In certain embodiments, the anoctamin is anoctamin-3 (ANO3). In certain embodiments, the anoctamin is anoctamin-4 (ANO4). In certain embodiments, the anoctamin is anoctamin-5 (ANO5). In certain embodiments, the anoctamin is anoctamin-6 (ANO6). In certain embodiments, the anoctamin is anoctamin-7 (ANO7). In certain embodiments, the anoctamin is anoctamin-8 (ANO8). In certain embodiments, the anoctamin is anoctamin-9 (ANO9). In certain embodiments, the anoctamin is anoctamin-10 (ANO10). In certain embodiments, the cancer or tumor expresses more than one anoctamin family member (e.g., ANO1 and ANO2).

In certain embodiments, the cancer or tumor treated by the methods and compositions described herein is brain cancer, nasopharyngeal carcinoma, breast cancer, lung cancer, hematopoietic cancers (e.g., leukemia, lymphoma, myeloma), colon cancer, liver cancer, stomach cancer, esophageal cancer, skin cancer, and bladder cancer.

In one embodiment, the subjection invention provides compositions and methods for treating brain cancer or a brain tumor in a subject, wherein the composition suppresses the expression level of ANO, preferably, ANO1. The subject invention provides compositions and methods for inhibiting the growth, and/or proliferation of brain tumor cells in a subject, wherein the composition suppresses the expression level of ANO, preferably, ANO1 in the brain tumor cells.

In one embodiment, the subjection invention provides compositions and methods for treating nasopharyngeal carcinoma in a subject, wherein the composition suppresses the expression of ANO, preferably, ANO1. The subject invention provides compositions and methods for inhibiting the growth, and/or proliferation of nasopharyngeal carcinoma cells in a subject, wherein the composition suppresses the expression level of ANO, preferably, ANO1 in the nasopharyngeal carcinoma cells.

In one embodiment, the subject invention provides compositions and methods for treating breast cancer in a subject, wherein the composition suppresses the expression level of ANO, preferably, ANO1. The subject invention provides compositions and methods for inhibiting the growth, and/or proliferation of breast cancer cells in a subject, wherein the composition suppresses the expression level of ANO, preferably, ANO1 in the breast cancer cells.

In one embodiment, the subjection invention provides compositions and methods for treating lung cancer in a subject, wherein the composition suppresses the expression level of ANO, preferably, ANO1. The subjection invention provides compositions and methods for inhibiting the growth, and/or proliferation of lung cancer cells in a subject, wherein the composition suppresses the expression level of ANO, preferably, ANO1 in the lung cancer cells.

In one embodiment, the subjection invention provides compositions and methods for treating leukemia in a subject, wherein the composition suppresses the expression level of ANO, preferably, ANO1. The subjection invention provides compositions and methods for inhibiting the growth, and/or proliferation of leukemia in a subject, wherein the composition suppresses the expression level of ANO, preferably, ANO1 in the leukemia.

In one embodiment, the subjection invention provides compositions and methods for treating lymphoma in a subject, wherein the composition suppresses the expression level of ANO, preferably, ANO1. The subjection invention provides compositions and methods for inhibiting the growth, and/or proliferation of lymphoma in a subject, wherein the composition suppresses the expression level of ANO, preferably, ANO1 in the lymphoma.

In one embodiment, the subjection invention provides compositions and methods for treating colon cancer in a subject, wherein the composition suppresses the expression level of ANO, preferably, ANO1. The subjection invention provides compositions and methods for inhibiting the growth, and/or proliferation of colon cancer in a subject, wherein the composition suppresses the expression level of ANO, preferably, ANO1 in the colon cancer.

In one embodiment, the subjection invention provides compositions and methods for treating liver cancer in a subject, wherein the composition suppresses the expression level of ANO, preferably, ANO1. The subjection invention provides compositions and methods for inhibiting the growth, and/or proliferation of liver cancer in a subject, wherein the composition suppresses the expression level of ANO, preferably, ANO1 in the liver cancer.

In one embodiment, the subjection invention provides compositions and methods for treating stomach cancer in a subject, wherein the composition suppresses the expression level of ANO, preferably, ANO1. The subjection invention provides compositions and methods for inhibiting the growth, and/or proliferation of stomach cancer in a subject, wherein the composition suppresses the expression level of ANO, preferably, ANO1 in the stomach cancer.

In one embodiment, the subjection invention provides compositions and methods for treating esophageal cancer in a subject, wherein the composition suppresses the expression level of ANO, preferably, ANO1. The subjection invention provides compositions and methods for inhibiting the growth, and/or proliferation of esophageal cancer in a subject, wherein the composition suppresses the expression level of ANO, preferably, ANO1 in the esophageal cancer.

In one embodiment, the subjection invention provides compositions and methods for treating bladder cancer in a subject, wherein the composition suppresses the expression level of ANO, preferably, ANO1. The subjection invention provides compositions and methods for inhibiting the growth, and/or proliferation of bladder cancer in a subject, wherein the composition suppresses the expression level of ANO, preferably, ANO1 in the bladder cancer.

In one embodiment, the subjection invention provides compositions and methods for treating skin cancer in a subject, wherein the composition suppresses the expression level of ANO, preferably, ANO1. The subjection invention provides compositions and methods for inhibiting the growth, and/or proliferation of skin cancer in a subject, wherein the composition suppresses the expression level of ANO, preferably, ANO1 in the skin cancer.

Cancers, cancer cells, and tumors treatable in accordance with the methods of the present invention may include, by way of example, primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory (e.g., androgen-independent prostate cancer; or hormone-refractory breast cancer, such as breast cancer that is refractory to tamoxifen); those that are refractory to treatment with one or more chemotherapeutic agents; those that are refractory to radiation; and those that are refractory to combinations of chemotherapy and radiation, chemotherapy and hormone therapy, or hormone therapy and radiation. In certain embodiments, the treatment inhibits tumor metastasis and/or other cancer cell migration.

In one embodiment, the method of treatment provided herein prevents tumorigenesis or carcinogensis in a subject. The subject method of treatment further provides methods for preventing tumorigenesis in a subject by administering an effective amount of the composition in the subject in need of such prevention.

Representative types of cancers, cancer cells and tumors treatable in accordance with the methods of the present invention include carcinomas, sarcomas, benign and malignant tumors, and malignancies. In general, the term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Adult tumors/cancers and pediatric tumors/cancers are included. The cancers may be vascularized, or not yet substantially vascularized, or non-vascularized tumors. Thus, the cancers may be characterized by non-solid tumors, e.g., hematopoietic cancers, such as leukemias and lymphomas (Hodgkins and non-Hodgkins), or solid tumors.

Exemplary cancers that can be treated according to the subject invention include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum);

pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva), osteogenic sarcoma, endotheliosarcoma, esophageal cancer, nasal cancer, medullary carcinoma, bile duct carcinoma, intestinal cancer, and hemangioblastoma. In preferred embodiments, the cancer or tumor is a brain tumor, nasopharyngeal carcinoma, breast cancer, lung cancer, leukemia, lymphoma, colon cancer, liver cancer, stomach cancer, esophageal cancer, skin cancer, and bladder cancer.

The therapeutically effective amounts may be provided on regular schedule, i.e., on a less than daily, daily, weekly, monthly, or yearly basis or on an irregular schedule with varying administration days, weeks, months, etc. Alternatively, the therapeutically effective amount to be administered may vary. In one embodiment, the therapeutically effective amount for the first dose may be higher than the therapeutically effective amount for one or more of the subsequent doses. In certain embodiments, the compositions described herein are administered on a continuous daily dosing schedule.

In another embodiment, the therapeutically effective amount for the first dose may be lower than the therapeutically effective amount for one or more of the subsequent doses. Equivalent dosages may be administered over various time periods including, for example, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of anti-cancer therapy will be determined according to the judgment of a healthcare practitioner.

Any of the methods provided herein may be used to treat cancer, cancer cells or tumors at any stage of development. Such stages include an advanced stage, a locally advanced stage, early stage cancer, progressive cancer, cancer in remission, relapsed cancer, and cancer that has proven refractory to other treatment (such as FDA-approved treatment). Accordingly, therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

In one embodiment, the composition may be administered orally, systemically or locally. In other embodiments, the composition is used to inhibit cancer cell growth, proliferation, and/or development ex vivo or in vitro. The therapeutic composition can also be administered via an enteral route or parenterally or topically or by inhalation.

In one embodiment, the subject invention provides a method for inhibiting carcinogenesis in a subject by administering a composition according to the subject invention. Carcinogenesis is the series of steps that take place as a normal cell becomes a cancer cell.

In one embodiment, the subjection invention provides compositions and methods for treating lung cancer in a subject. The subjection invention provides compositions and methods for inhibiting the growth of lung cancer cells in a subject. The lung cancer includes, for example, small cell lung cancer, lung adenocarcinoma, squamous cell lung carcinoma, large cell lung carcinoma, carcinoids, adenoid cystic carcinoma, mucoepidermoid carcinoma, malignant mixed tumor and the like. Among them, examples in which the composition for treating lung cancer of the invention exhibit preferred effect include small cell lung cancer, lung adenocarcinoma, squamous cell lung carcinoma, large cell lung carcinoma and the like, and particularly preferred one is small cell lung cancer.

In one embodiment, the subjection invention provides compositions and methods for treating breast cancer in a subject. The subjection invention also provides compositions and methods for inhibiting the growth of breast cancer cells in a subject.

In one embodiment, the subjection invention provides compositions and methods for treating colon cancer in a subject. The subjection invention also provides compositions and methods for inhibiting the growth of colon cancer cells in a subject.

In one embodiment, the subject invention provides a pharmaceutical composition and method for treating gastrointestinal cancer, particularly in the villous region and the brush border, and/or associated with the alteration of absorptive capacity in the small intestine.

In other embodiments, the composition and methods described herein are useful for skin cancer. In this embodiment, the methods of the subject invention generally include the step of topically applying the compositions to the skin (e.g., epidermis) of the patient needing such treatment, wherein a therapeutically effective amount of such composition is applied.

The term "topical application," as used herein, means to apply or spread the compositions of the present invention onto the surface of the epidermis tissue.

Methods of Inhibiting Cancer Cell Growth

Also provided herein are methods of inhibiting cancer cell growth comprising exposing cancer cells to the compositions described herein. For example, the compositions may comprise one or more free amino acids selected from proline, serine, threonine, tyrosine, valine, asparagine, glycine, tryptophan, lysine, leucine, phenylalanine, methionine, arginine, histidine, and cysteine, and a pharmaceutically acceptable excipient.

In certain embodiments, the one or more free amino acids comprise, consist essentially of, or consist of proline, serine, threonine, tyrosine, and valine. In certain embodiments, the one or more free amino acids comprise, consist essentially of, or consist of proline, serine, threonine, tyrosine, valine, asparagine, and glycine.

In other embodiments, the compositions provided herein do not include, or include only negligible amounts of, one or more free amino acids selected from glutamate, glutamine, aspartic acid, alanine and isoleucine. In certain embodiments, the compositions provided herein do not include, or include only negligible amounts of, the free amino acids glutamate, glutamine, aspartic acid, alanine, and isoleucine.

In one embodiment, the methods lead to an inhibition of cancer cell growth and/or death of cancer cells. In one embodiment, the method comprises introducing the composition according to the present invention to cancer cells in culture for inhibiting the growth, proliferation, and/or development. The composition may thus be used to treat various tumors and cancers.

When the composition is applied to cancer cells either in culture, or in situ, changes occur in these cells at for example, cellular, and molecular levels. As a result, the cellular activity may be altered.

Examples of cancers that could serve as sources of cancer cells include solid tumors such as those derived from, for example, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; vulvar cancer (e.g., Paget's disease of the vulva); and nasal cancer.

Additional cancers that may serve as sources of cancer cells include blood borne cancers such as hematopoietic cancers (e.g., leukemia such as acute promyelocytic leukemia ("APL"), acute monoblastic leukemia, acute erythroleukemic leukemia, acute megakaryoblastic leukemia, acute nonlymphocytic leukemia, acute undifferentiated leukemia, acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., Waldenstrom's macroglobulinemia, B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); and myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)).

EXAMPLES

The following examples are provided to further describe some of the embodiments disclosed herein. The examples are intended to illustrate, not to limit, the disclosed embodiments.

Example 1

Radiation increases Anocatmin-1 (ANO1) Expression

FIG. 1 shows a Western blots analysis of anocatmin-1 (ANO1) protein levels following exposure to 0, 0.5, 1, 3, 5, 7 and 9 Gy of radiation and following exposure to 0 and 5Gy of radiation in the presence and absence of an amino acid oral rehydration solution (AA-ORS).

Figure 2:
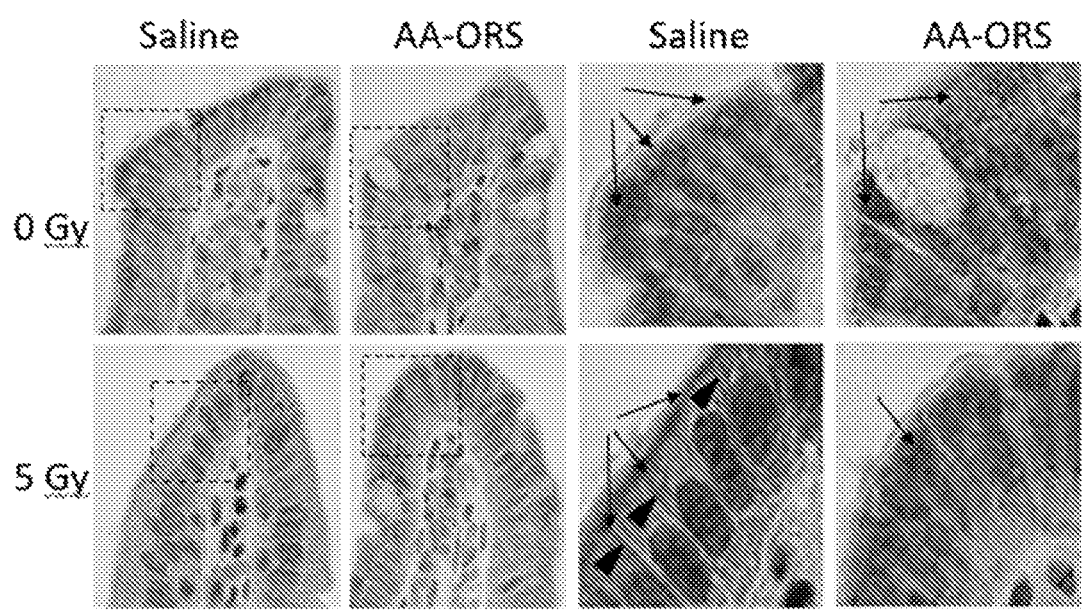
FIG. 2 illustrates the effect of radiation on ANO1 expression along the brush border membrane of the small bowel after exposure to 0 or 5 Gy of radiation in the presence of a saline or AA-ORS solution.

FIG. 2 illustrates the effect of radiation on ANO1 expression along the brush border membrane of the small bowel after exposure to 0 or 5Gy of radiation in the presence of a saline or AA-ORS solution.

Example 2

Downregulation of ANO1 Expression with siRNA Inhibits the Growth of Cancer Cells but not Normal Cells It is known that ANO1 has the ability to regulate cell shape and volume, and contributes to cell movement and metastasis. To investigate the effect of blocking anoctamin expression on cancer cells, colony-forming assay is performed using siRNA.

Figure 3:
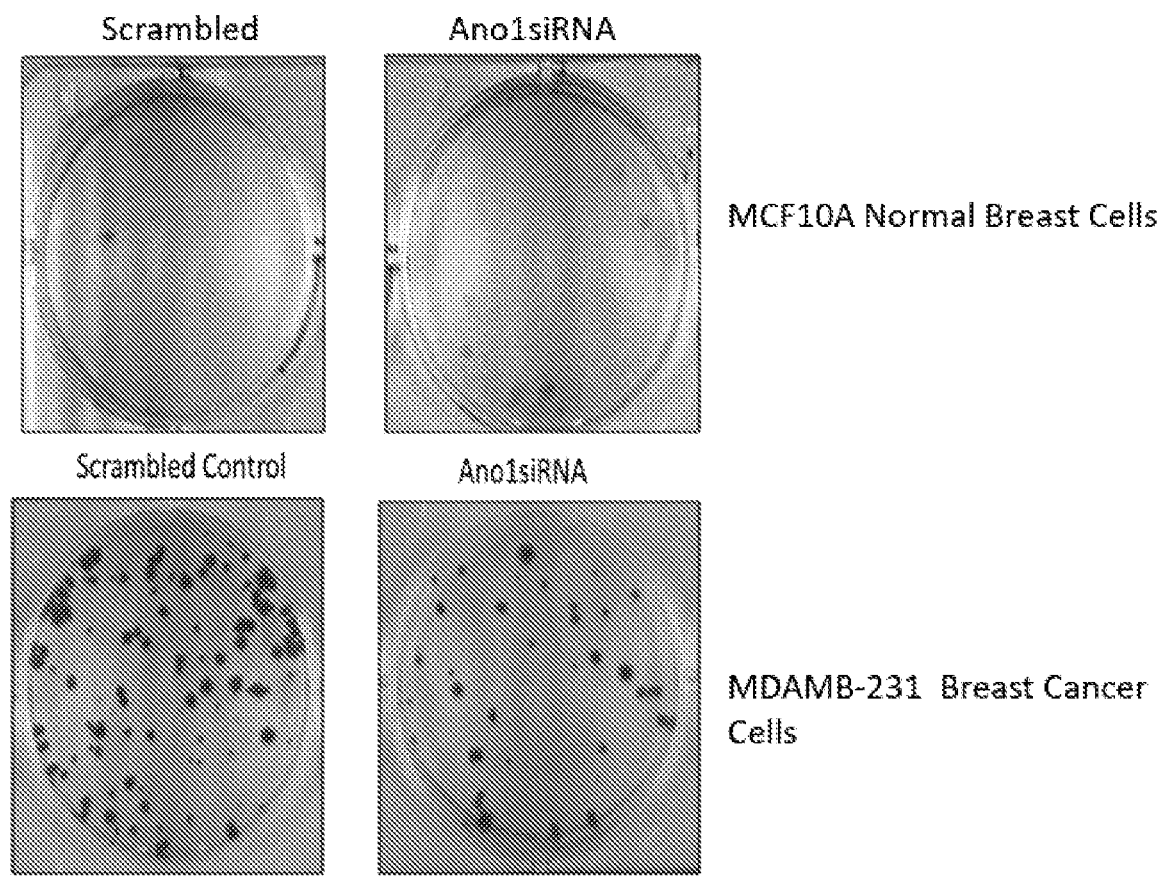
FIG. 3 illustrates the effect of a scrambled control siRNA and ANO1 siRNA on MCF10A normal breast cells and MDAMB-231 breast cancer cells in a clonogenic assay.

FIG. 3 illustrates the effect of a scrambled control siRNA and ANO1 siRNA on MCF10A normal breast cells and MDAMB-231 breast cancer cells in a clonogenic assay.

Figure 4:
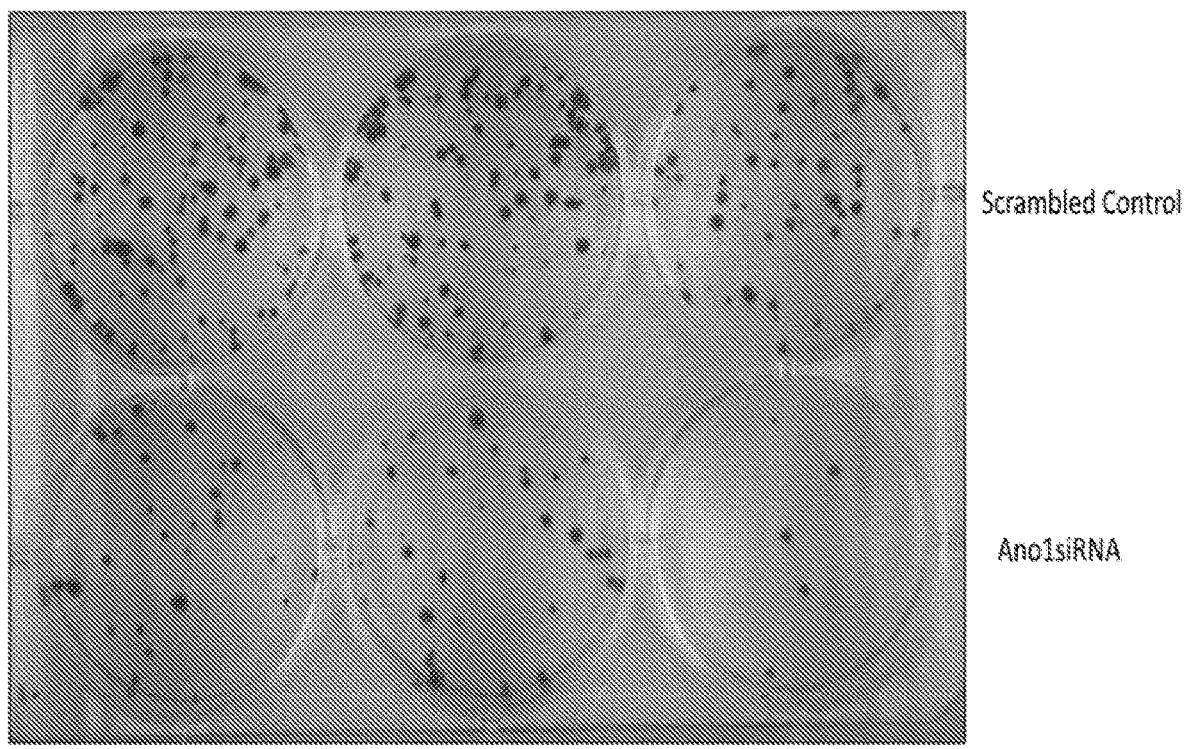
FIG. 4 further illustrates the effect of a scrambled control siRNA and ANO1 siRNA on MDAMB-32 breast cancer cells in a clonogenic assay.

FIG. 4 further illustrates the effect of a scrambled control siRNA and ANO1 siRNA on MDAMB-32 breast cancer cells in a clonogenic assay.

Figure 5:
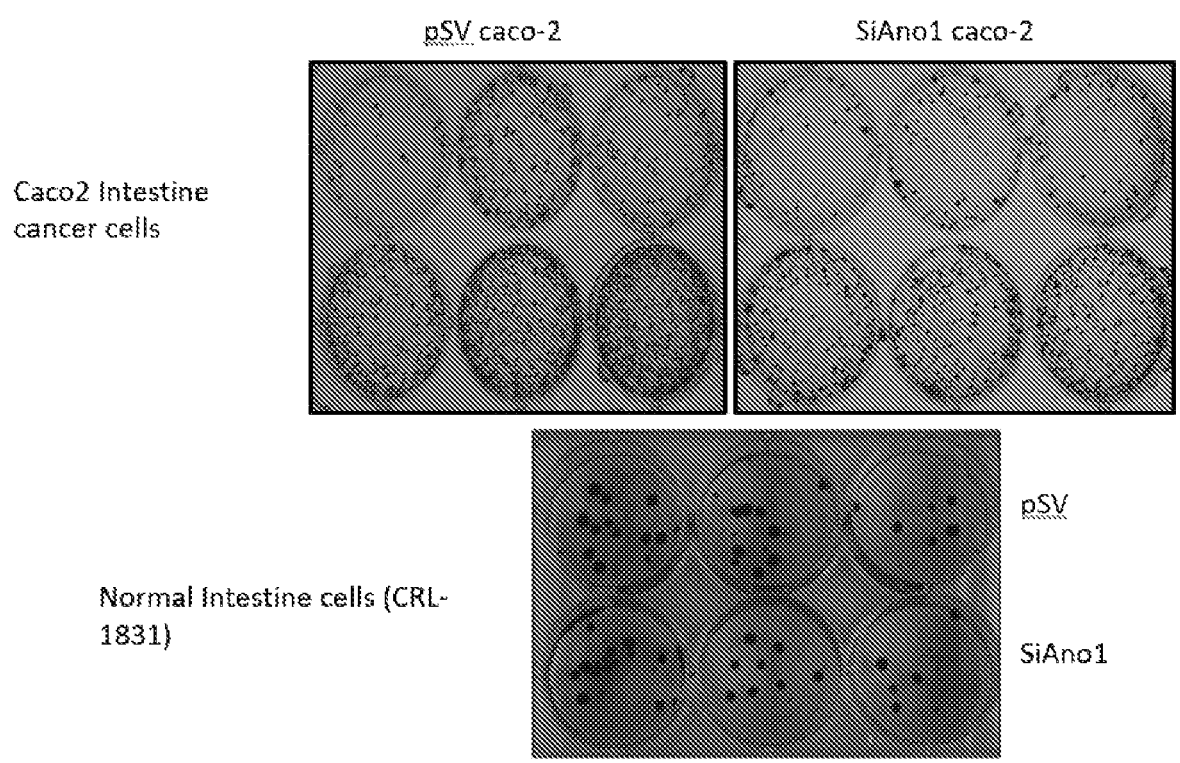
FIG. 5 illustrates the effects of a control plasmid vector pSV caco-2 and ANO1 siRNA in Caco2 intestine cancer cells and on normal intestinal cells (CRL-1831) in a clonogenic assay.

FIG. 5 illustrates the effects of a control plasmid vector pSV caco-2 and ANO1 siRNA in Caco2 intestine cancer cells and on normal intestinal cells (CRL-1831) in a clonogenic assay.

Figure 6:
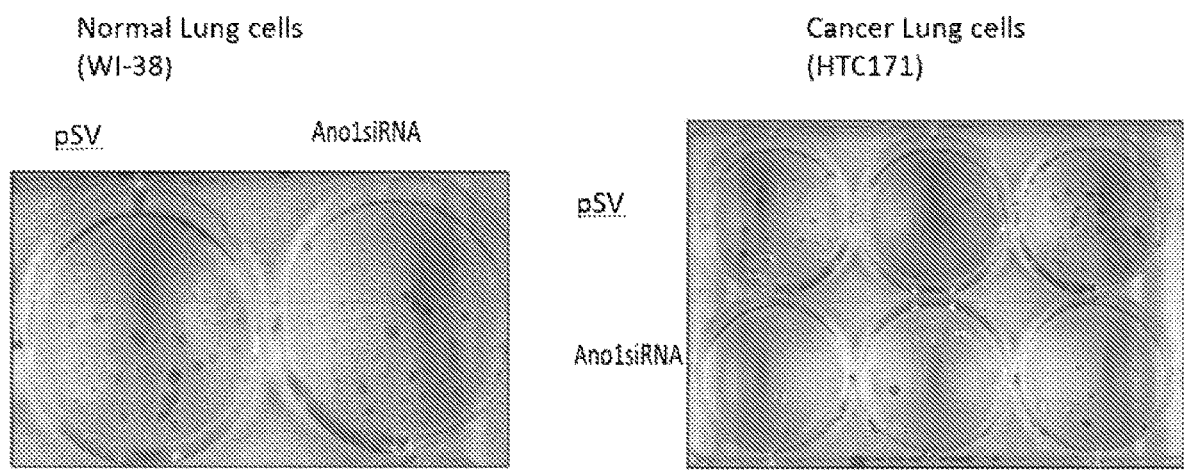
FIG. 6 illustrates the effect of a control plasmid vector (pSV) and ANO1 siRNA on normal lung cells (WI-38) and on cancer lung cells (HTC171) in a clonogenic assay.

FIG. 6 illustrates the effect of a control plasmid vector (pSV) and ANO1 siRNA on normal lung cells (WI-38) and on cancer lung cells (HTC171) in a clonogenic assay.

The protocol for the clonogenic assay (cell lines and culture conditions) is as follows. The following human cell lines are used: HFL-1 (Human Lung Fibroblasts-1), and HDFn (Human Dermal Fibroblasts); (ATCC; Manassas, USA). HFL-1 cells are cultured in F-12K Medium (Kaighn's Modification of Ham's F-12 Medium) supplemented with 10% fetal bovine serum (FBS) and 10 mg/mL penicillin/streptomycin at 37° C. in a humidified incubator gassed with 95% O2 and 5% CO2. HDFn cells are cultured in fibroblast basal media (ATCC) supplemented with 5 ng/mL FGFb, 7.5 mM L-Glutamine, 50 mg/mL Ascorbic acid, 1mg/mL hydrocortisone, 5 mg/mL insulin and 2% FBS (Sigma Aldrich, St. Louis, MO, USA).

Cell concentrations in the culture are adjusted to allow exponential growth.

Plating density

Cells are plated in 6-well, flat bottom culture plates (Denville Scientific Inc.) at a density of 500 cells/well to allow forming of single colonies.

Colony evaluation

After 14 days, media is removed and cells are rinsed with PBS. Colonies are fixed and stained for 30 min in 0.5% crystal violet diluted in 50/50 methanol/water. Dishes are rinsed with water and left to dry at room temperature.

Figure 10A:
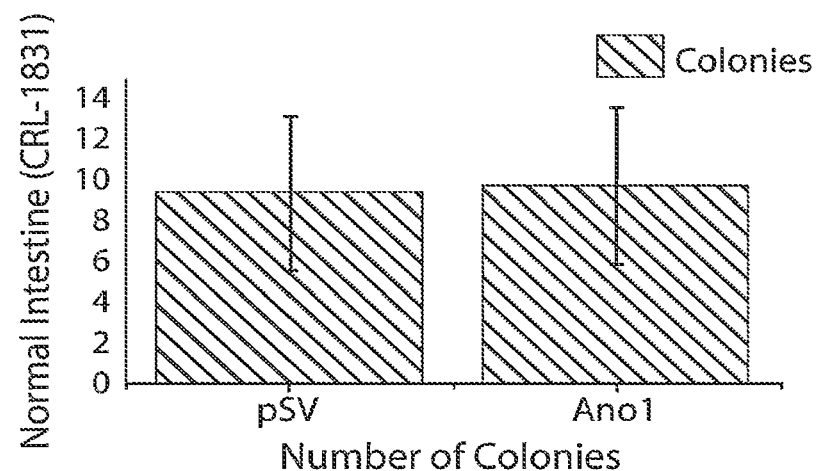
FIGS. 10A and 10B show the effects of a control plasmid vector pSV caco-2 and ANO1 siRNA in Caco2 intestine cancer cells and on normal intestinal cells (CRL-1831) in a clonogenic assay (also shown in FIG. 5).
Figure 10B:
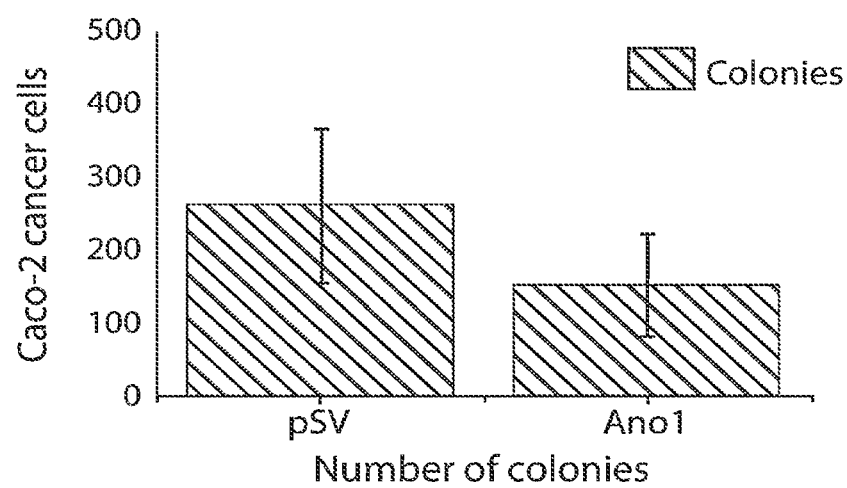

Positive colonies (>50 cells/colony) are counted by Image J software, and survival fraction (SF) is calculated as described elsewhere. The results are based on three repeats. (See Franken N A, Rodermond H M, Stap J, Haveman J, van Bree C. Clonogenic assay of cells in vitro. Nat Protoc. 2006; 1:2315-2319. doi: 10.1038/nprot.2006.339.). Results of the clonogenic assay are depicted in FIGS. 5 and 10.

Example 3

Exemplary Amino Acids Decrease the Expression of ANO1

All 20 exemplary amino acids are evaluated for their ability to decrease ANO1 protein expression in cells of the brush border membrane.

Figure 7:
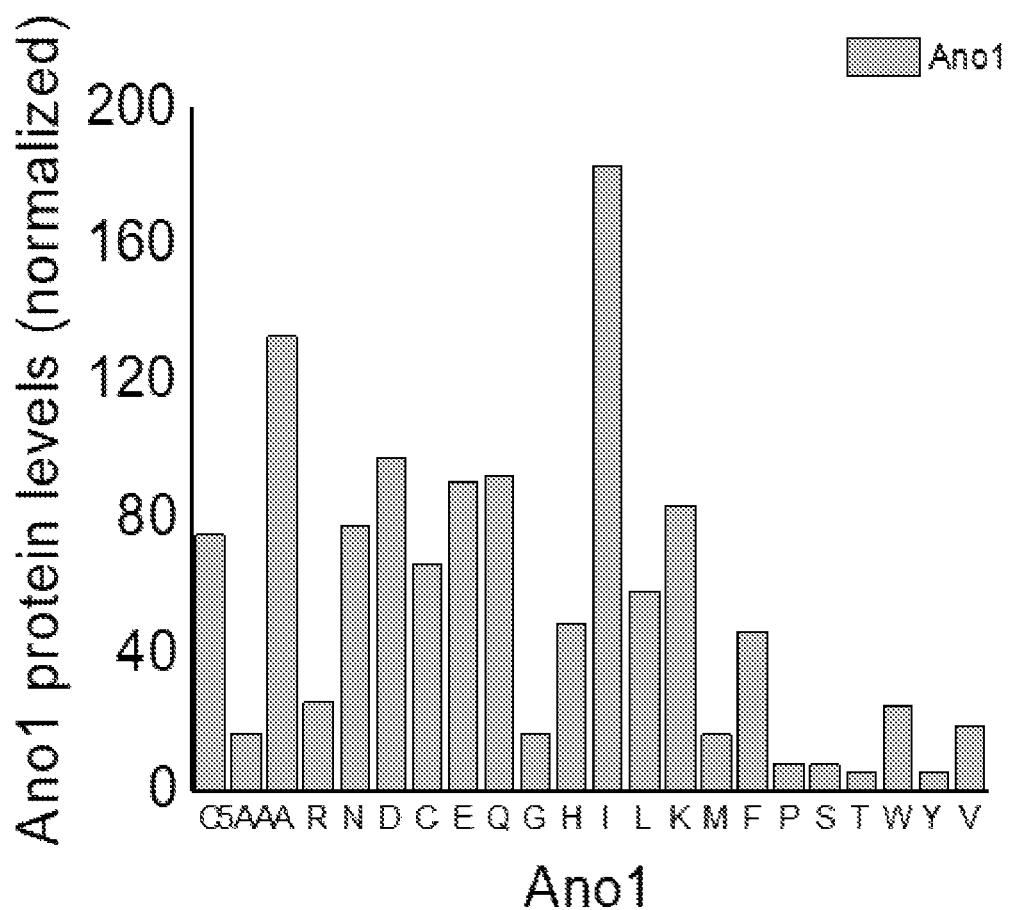
FIG. 7 illustrates the normalized effect of individual exemplary amino acids, a control protein, and a combination of five amino acids (5AA) on Ano1 protein levels.
Figure 8:
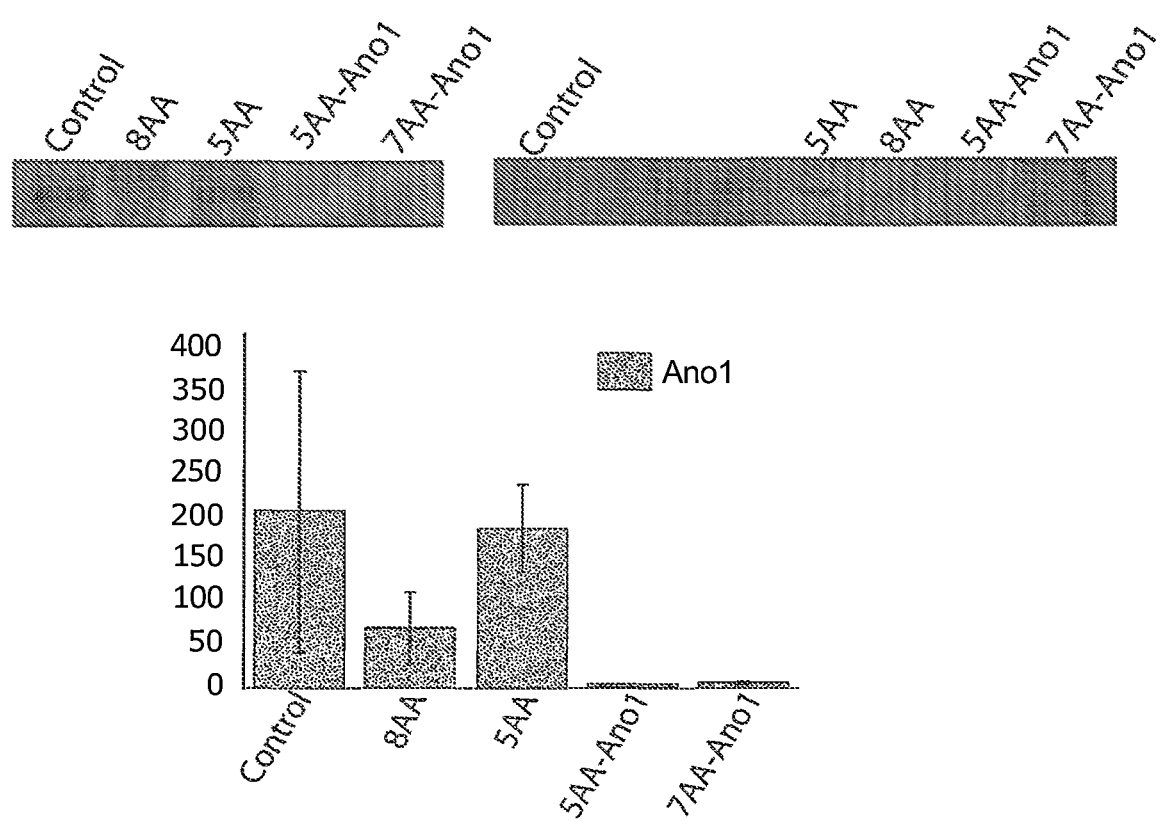
FIG. 8 shows a Western blot analysis of protein levels of ANO1 protein extracted from cells of the brush border membrane following treatment with a control protein, a combination of eight amino acids (8AA) (Isoleucine, Aspartic acid, Threonine, Lysine, Tyrosine, Serine, Valine, Glycine, Tryptophan), a combination of five amino acids (5AA), another combination of five amino acids (5AA-Ano1), and a combination of seven amino acids (7AA-Ano1).
Figure 9A:
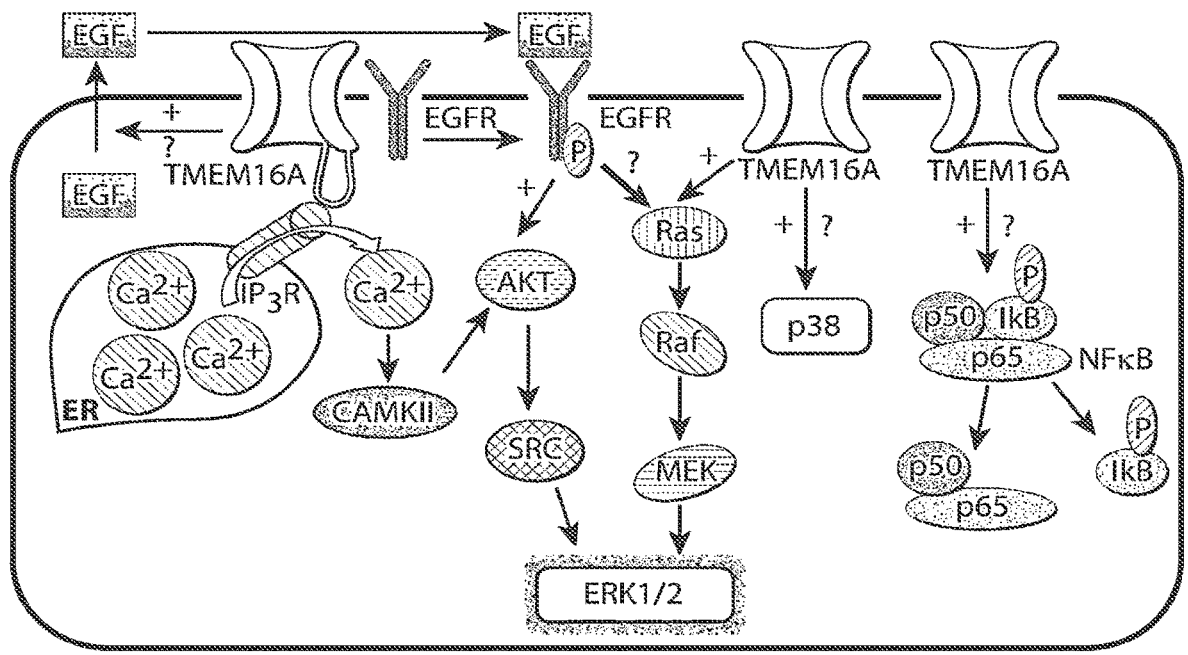
FIG. 9A shows signaling pathways activated by Anoctamin-1.
Figure 9B:
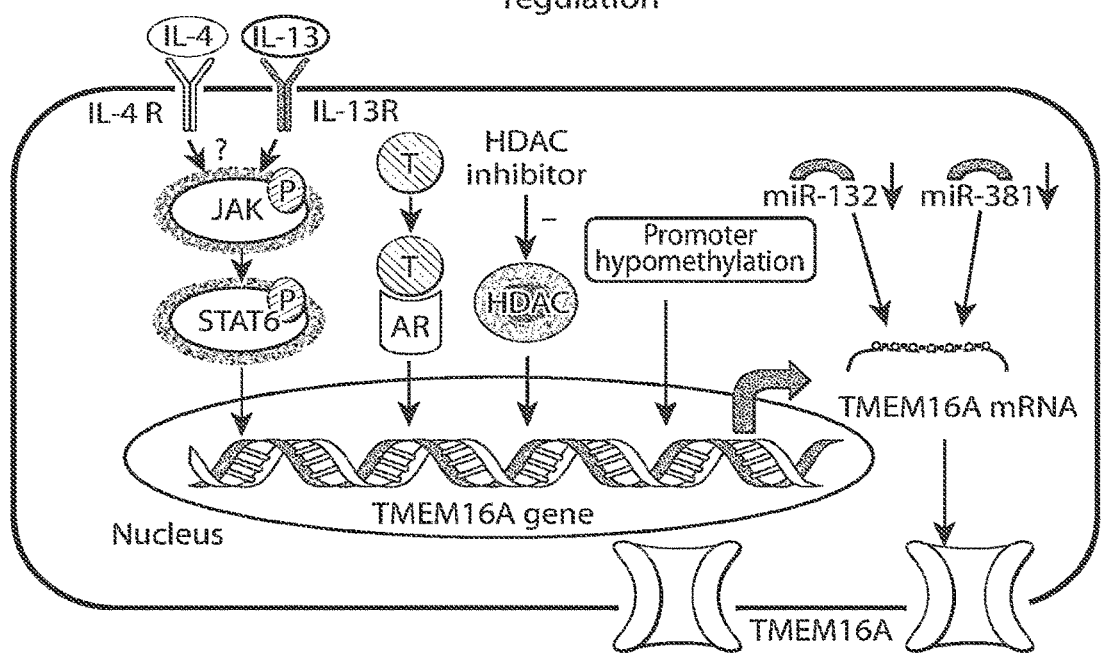
FIG. 9B shows a diagram of the regulation of Ano1.

FIG. 7 shows a Western blot analysis of protein levels of ANO1 protein extracted from cells of the brush border membrane following treatment with a control protein, a combination of eight amino acids (8AA), a combination of five amino acids (5AA), another combination of five amino acids (5AA-Ano1), and a combination of seven amino acids (7AA-Ano 1).

Example 4

Effects of Exemplary Amino Acids in ANO1 Inhibition and Cancer

Figure 11A:
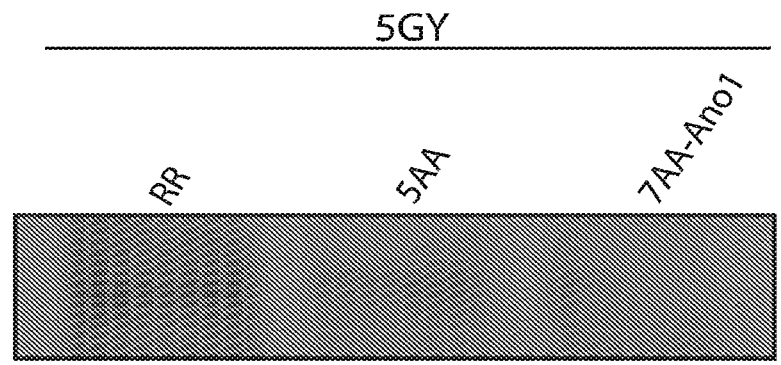
FIG. 11A shows a Western blot analysis of anocatmin-1 (ANO1) protein levels following exposure of 5Gy of radiation (and treated with regular ringer solution ("RR") "5AA" (Aspartic Acid, Serine, Tyrosine, Threonine, and Valine), or "7AA-ANO1" (proline, serine, threonine, tyrosine, valine, asparagine and glycine). Treatment with 5AA inhibited ano1 expression on the brush border membrane isolated from intestinal epithelial cells. Treatment with 7AA-ANO1, the amino acids that specifically inhibited ano1 expression on the cell membrane, further decreased the protein level in the brush border membrane.
Figure 11B:
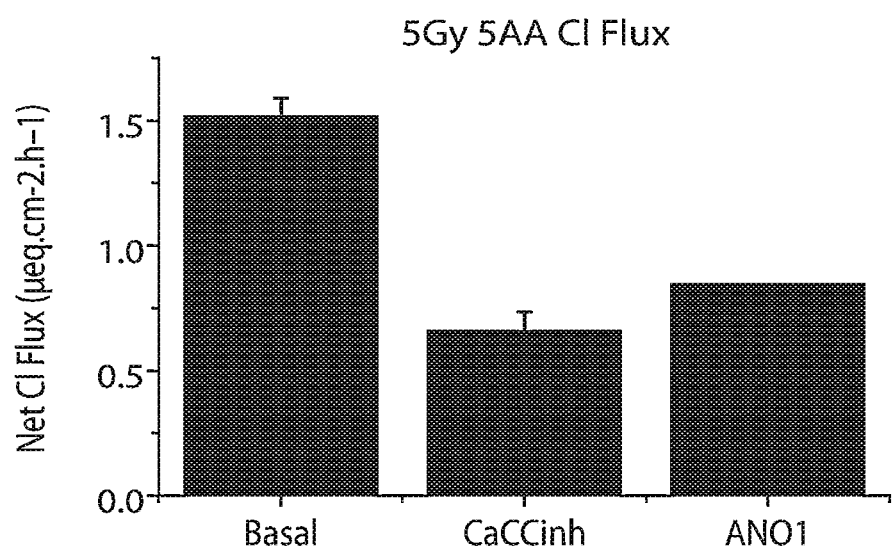
FIG. 11B shows the net flux of Cl-following exposure of 5Gy of radiation and treatment with "5AA," at basal levels, specific inhibitor of ANO1 (CaCCinh, and "ANO1.
Figure 11C:
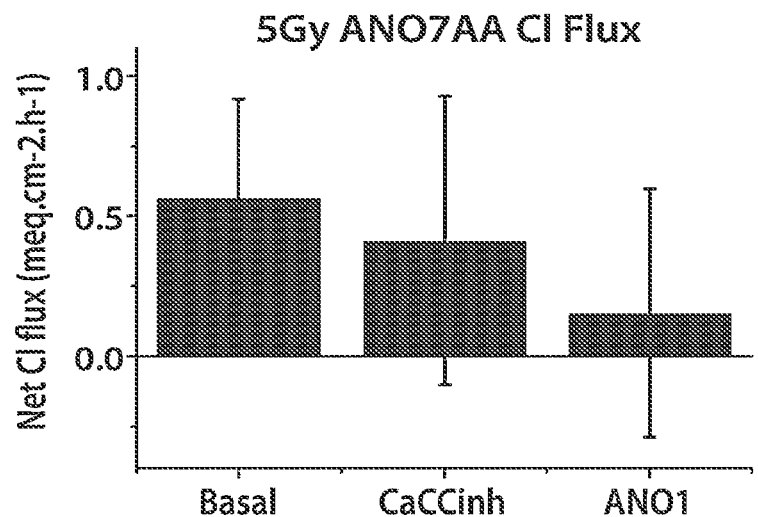
Figure 12:
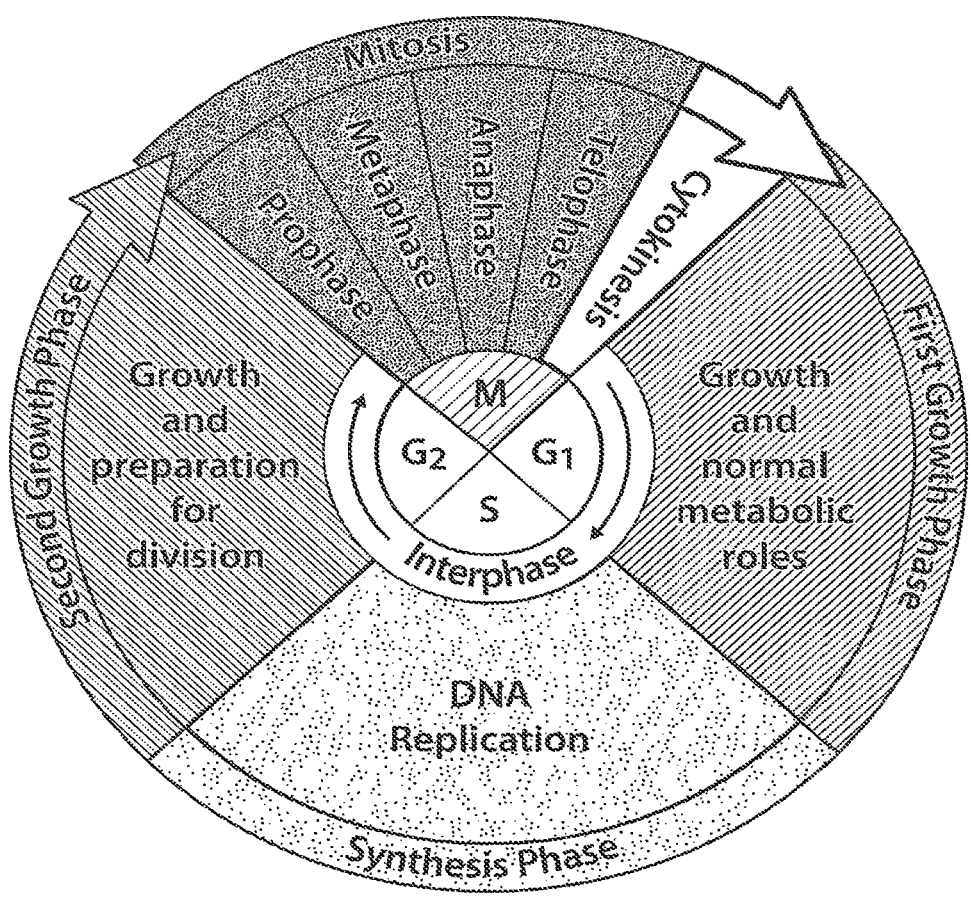
FIG. 12 shows a diagram of the cell cycle. Propidium iodide (PI) staining for cell cycle was conducted as follows: Diploid cells in G1 phase will have 2N chromosomes—in other words, half the amount of cells in G2 or M phase, which have a 4N chromosomal complement. Cells in S phase, which are in the process of synthesizing new chromosomes (new DNA) have an intermediate amount. Since PI will label the cells in proportion to their DNA content, the percentage of cells in each phase can be read off a histogram.
Figure 13A:
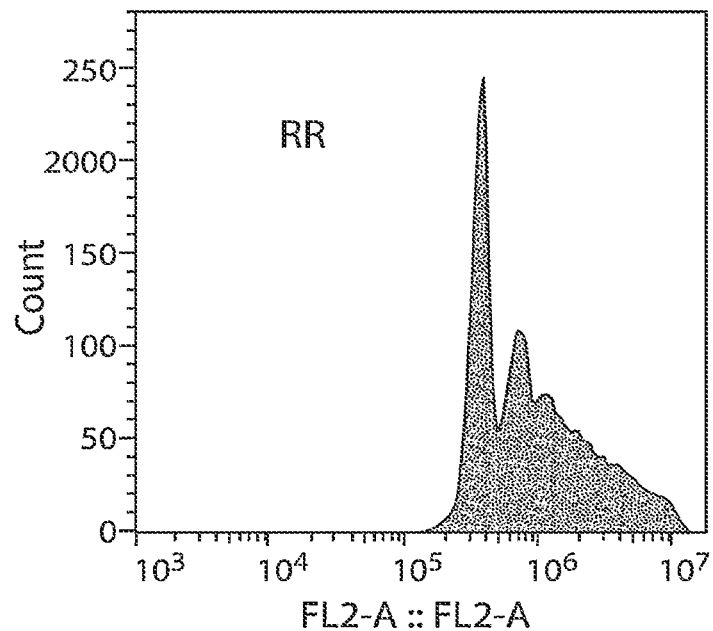
FIGS. 13A-13D show the effects of a 4 hour treatment of the indicated amino acid compositions on colon cancer cells (HT-29).
Figure 13B:
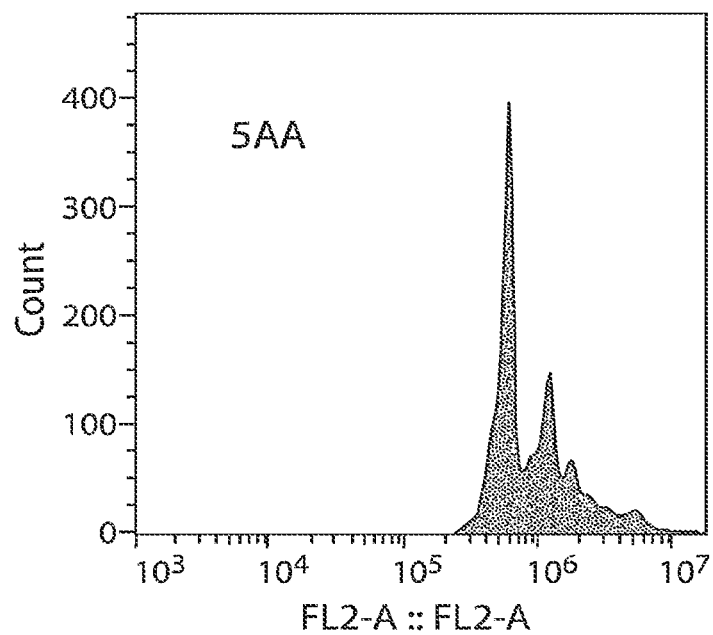
Figure 13C:
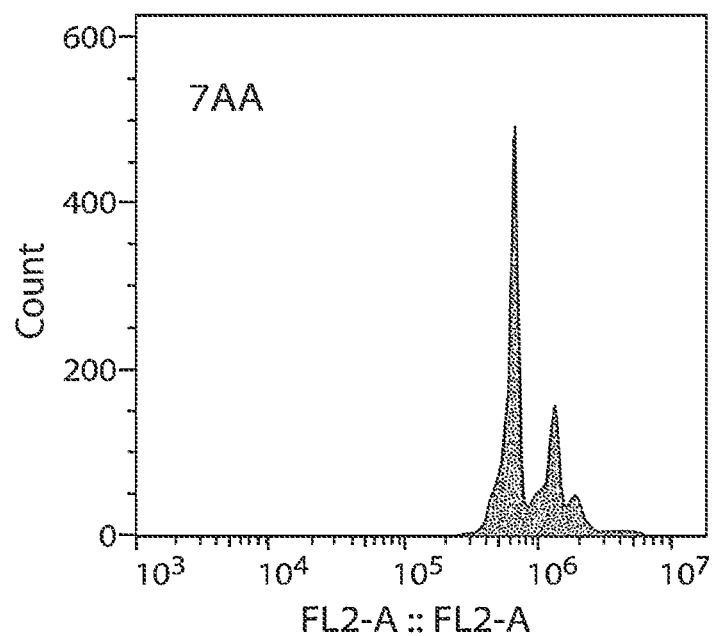
Figure 13D:
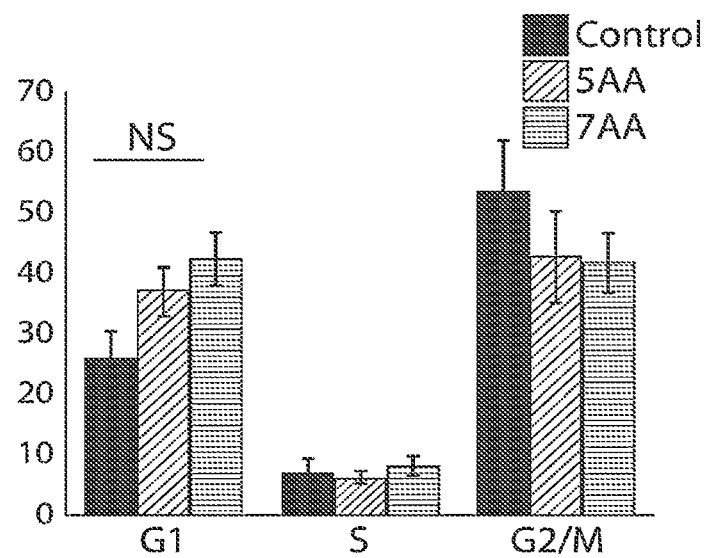

A study was conducted to examine anocatmin-1 (ANO1) protein levels following exposure of 5Gy of radiation (and treated with "RR," "5AA," or "7AA-ANO1." Treatment with 5AA inhibited ano1 expression on the brush border membrane isolated from intestinal epithelial cells (FIG. 11A). Treatment with 7AA-ANO1, the amino acids that specifically inhibited ano1 expression on the cell membrane, further decreased the protein level in the brush border membrane (FIG. 11A). Ussing chamber flux studies show that specific inhibitor of ANO1 (CaCCinh) decreased net chloride flux and the 7 amino acids that decreased ano1 expression (ANO7AA) on the membrane similarly decreased net chloride flux (FIGS. 11B and 11C). The flux was studied using 36Cl an isotope for chloride.

The effects of treatment of particular amino acid compositions (regular ringer solution ("RR"), 5AA, and 7AA) was also examined via a study, on the arrest of cells in the particular phases G1, S, and G2/M in the cell cycle in colon cancer cells (HT-29). Flow cytometry (FACS) was conducted using cells incubated in the presence of regular ringer solution ("RR"), 5AA, and 7AA for four hours in colon cancer cells (HT-29). 7AA inhibits the cells in G2/M phase and therefore there are more cell numbers arrested in G1 phase (FIGS. 13A-D).

Figure 14:
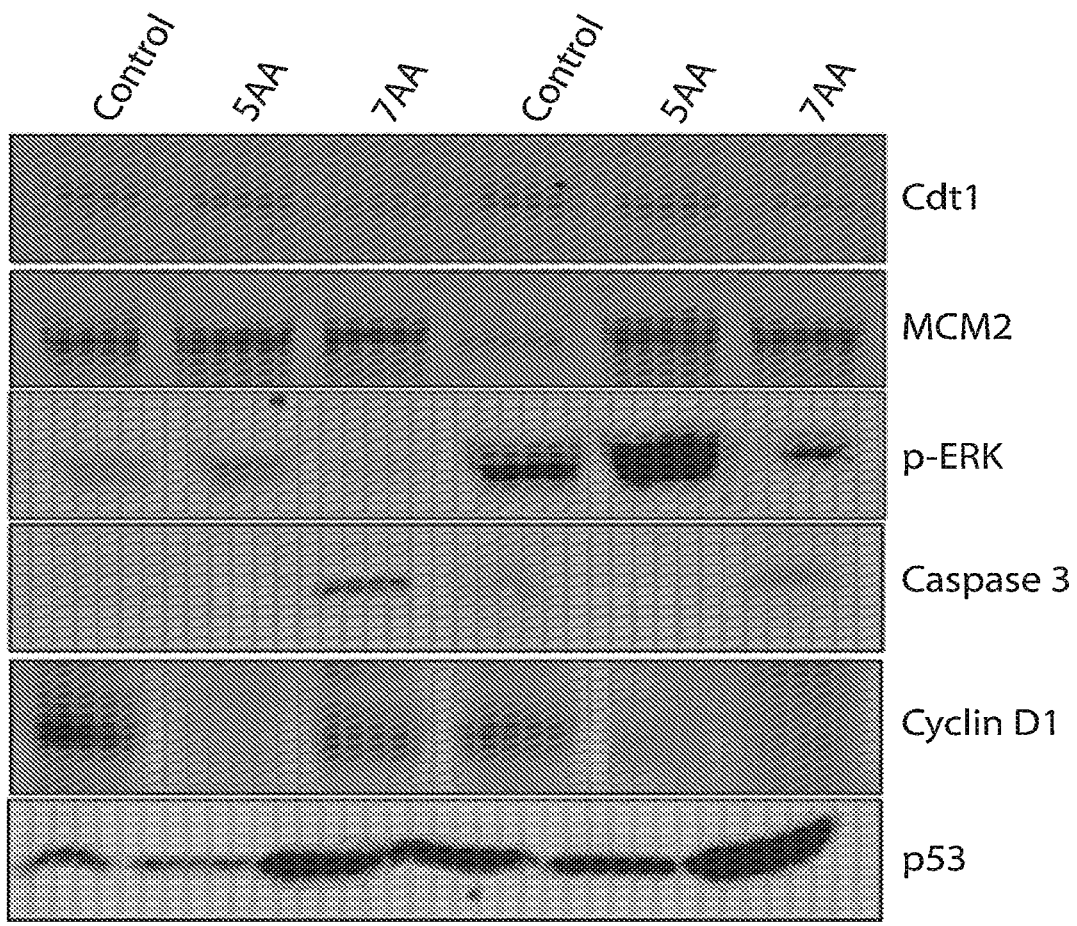
FIG. 14 shows the effects of a 4 hour treatment of control, 5AA, and 7AA on HT-29 colon cancer cells, on the binding of CDT1, MCM2, p-ERK, Caspase 3, cyclin D1, and p53. The origin recognition complex (ORC) is thought to be bound to chromatin throughout the cell cycle (1,2). The prereplication complex (Pre-RC) forms in late mitosis/early G1 phase beginning with the binding of CDT1 and cdc6 to the origin, which allows binding of the heterohexameric MCM2-7 complex. The MCM complex is thought to be the replicative helicase, and formation of the pre-RC is referred to as chromatin licensing.

The effects of a 4 hour treatment of control, 5AA, and 7AA were examined in HT-29 colon cancer cells, on the binding of CDT1, MCM2, p-ERK, Caspase 3, cyclin D1, and p53 (FIG. 14). The origin recognition complex (ORC) is thought to be bound to chromatin throughout the cell cycle (1,2). The prereplication complex (Pre-RC) forms in late mitosis/early G1 phase beginning with the binding of CDT1 and cdc6 to the origin, which allows binding of the heterohexameric MCM2-7 complex. The MCM complex is thought to be the replicative helicase, and formation of the pre-RC is referred to as chromatin licensing. See FIG. 14.

Figure 15A:
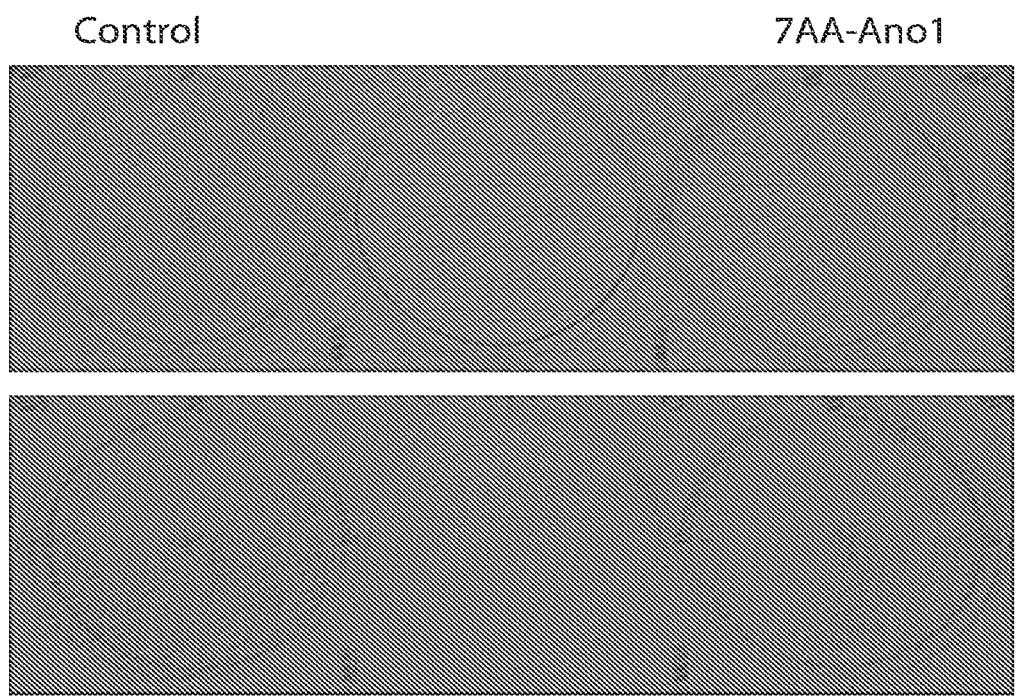
FIG. 15A shows the effects of treatment of HT-29 colon cancer cells with control and 7AA-ANO1 under a 4-hour treatment described as follows. The top seven amino acids that decrease ANO1 protein levels in the brush border membrane of the cells when used in combination (7AA-Ano1) was shown to decrease the number of colony formation when compared to control. The cells were incubated in the presence of the 7 AA for a period of 4 hours and then washed off and grown further in the presence of regular culture media. These studies show that the 7 AA can inhibit the tumor cells and may work via a signaling mechanism.
Figure 15B:
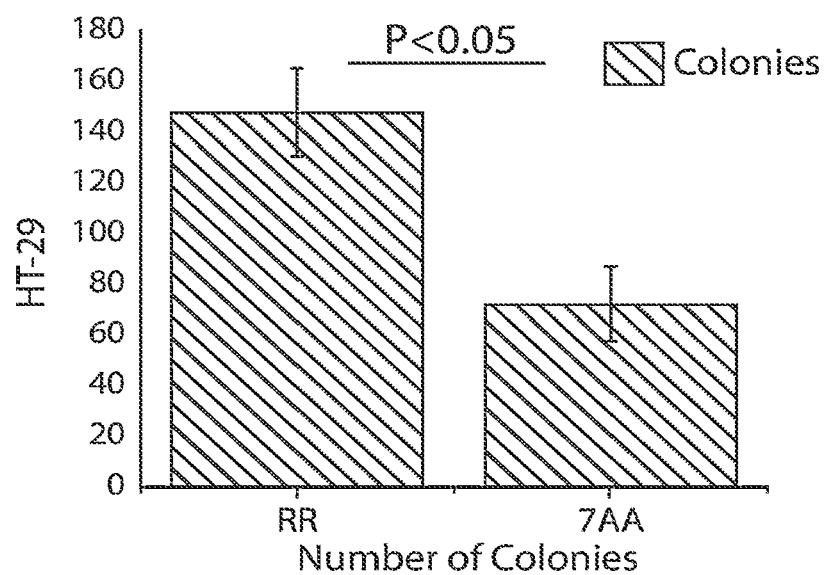
FIG. 15B shows the number of colonies upon the treatment described above for FIG. 15A with regular ringer solution (RR) and 7AA.

The effects of treatment of HT-29 colon cancer cells with control and 7AA-ANO1 under a 4-hour treatment were analyzed as follows. The top seven Amino acids that decrease ANO1 protein levels in the brush border membrane of the cells when used in combination (7AA-Ano1) was shown to decrease the number of colony formation when compared to control. The cells were incubated in the presence of the 7 AA for a period of 4 hours and then washed off and grown further in the presence of regular culture media. These studies show that the 7 AA can inhibit the tumor cells and may work via a signaling mechanism (FIGS. 15A and 15B). There were a decreased number of colonies upon the treatment described above for FIG. 15A with regular ringer solution (RR) and 7AA (FIG. 15B).

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed is:

1. A formulation for inhibiting proliferation of cancer cells comprising:
   a therapeutically effective amount of free amino acids, the free amino acids consisting essentially of or consisting of free amino acids of:
   proline, serine, threonine, tyrosine, and valine; or
   proline, serine, threonine, tyrosine, valine, asparagine, and glycine; and
   optionally a pharmaceutically acceptable carrier, buffer, electrolyte, adjuvant, or excipient;
   wherein a therapeutically effective amount of the formulation inhibits proliferation of cancer cells.

2. The formulation of claim 1, wherein the formulation does not comprise free amino acids of glutamate, glutamine, aspartic acid, alanine, or isoleucine, or any combination thereof; or
when the formulation does comprise free amino acids of glutamate, glutamine, aspartic acid, alanine, or isoleucine, or any combination thereof, the free amino acids of glutamate, glutamine, aspartic acid, alanine, or isoleucine, or any combination thereof are present in negligible amounts.

3. The formulation of claim 1, wherein the cancer cells express anoctamin (ANO), wherein the ANO is anoctamin-1 (ANO-1).

4. A method of treating cancer expressing anoctamin (ANO) in a subject in need thereof, the method comprising administering to the subject in need thereof a therapeutically effective amount of a formulation comprising:
   a therapeutically effective amount of free amino acids, the free amino acids consisting essentially of or consisting of free amino acids of:
   proline serine, threonine, tyrosine, and valine; or
   proline, serine, threonine, tyrosine, valine, asparagine, and glycine; and
   optionally a pharmaceutically acceptable carrier, buffer, electrolyte, adjuvant, or excipient;
   wherein the cancer expressing ANO comprises cancer cells and a therapeutically effective amount of the formulation inhibits proliferation of the cancer cells.

5. The method of claim 4, wherein the formulation does not comprise free amino acids of glutamate, glutamine, aspartic acid, alanine, or isoleucine, or any combination thereof, or
when the formulation does comprise free amino acids of glutamate, glutamine, aspartic acid, alanine, or isoleucine, or any combination thereof, the free amino acids of glutamate, glutamine, aspartic acid, alanine, or isoleucine are present in negligible amounts.

6. The method of claim 4, wherein the ANO is anoctamin-1 (ANO-1).

7. The method of claim 4, wherein the cancer comprises nasopharyngeal carcinoma, breast cancer, lung cancer, colon cancer, esophageal cancer, or bladder cancer.

8. A method of inhibiting cancer cell proliferation comprising exposing cancer cells expressing anoctamin (ANO) to a formulation comprising:
   an effective amount of free amino acids, the free amino acids consisting essentially of or consisting of free amino acids of:
   proline, serine, threonine, tyrosine, and valine; or
   proline, serine, threonine, tyrosine, valine, asparagine, and glycine; and
   optionally a pharmaceutically acceptable carrier, buffer, electrolyte, adjuvant, or excipient;
   wherein the effective amount of the free amino acids inhibits proliferation of the cancer cells expressing ANO.

9. The method of claim 8, wherein the formulation does not comprise free amino acids of glutamate, glutamine, aspartic acid, alanine, or isoleucine, or any combination thereof; or
when the formulation does comprise free amino acids of glutamate, glutamine, aspartic acid, alanine, or isoleucine, or any combination thereof, the free amino acids of glutamate, glutamine, aspartic acid, alanine, or isoleucine are present in negligible amounts.

10. A method of downregulating anoctamin (ANO) expression in at least one cancer cell, the method comprising contacting the at least one cancer cell with an effective amount of a formulation of claim 1,
   wherein the therapeutically effective amount of the free amino acids downregulates ANO expression in the at least one cancer cell.

11. The method of claim 10, wherein the formulation does not comprise free amino acids of glutamate, glutamine, aspartic acid, alanine, or isoleucine, or any combination thereof.

12. The method of claim 10, wherein the anoctamin is ANO1.

* * * * *